United States Patent
Swisher et al.

(10) Patent No.: US 11,984,224 B2
(45) Date of Patent: May 14, 2024

(54) MACHINE LEARNING ON RAW MEDICAL IMAGING DATA FOR CLINICAL DECISION SUPPORT

(71) Applicant: KONINKLIJKE PHILIPS N.V., Eindhoven (NL)

(72) Inventors: Christine Menking Swisher, San Diego, CA (US); Homer Pien, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 494 days.

(21) Appl. No.: 16/616,664

(22) PCT Filed: May 30, 2018

(86) PCT No.: PCT/EP2018/064308
§ 371 (c)(1),
(2) Date: Nov. 25, 2019

(87) PCT Pub. No.: WO2018/220089
PCT Pub. Date: Dec. 6, 2018

(65) Prior Publication Data
US 2021/0174937 A1 Jun. 10, 2021

Related U.S. Application Data

(60) Provisional application No. 62/512,774, filed on May 31, 2017.

(51) Int. Cl.
*G06T 7/12* (2017.01)
*G06F 18/213* (2023.01)
(Continued)

(52) U.S. Cl.
CPC ........... *G16H 50/20* (2018.01); *G06F 18/213* (2023.01); *G06T 11/003* (2013.01); *G16H 30/40* (2018.01)

(58) Field of Classification Search
CPC ...... G16H 30/40; G16H 50/20; G06K 9/6232; G06T 11/003; G06T 7/12
See application file for complete search history.

(56) References Cited

U.S. PATENT DOCUMENTS 8,735,074 B2 5/2014 Mambo
9,347,945 B2 5/2016 Colpitts
(Continued)

FOREIGN PATENT DOCUMENTS

WO WO2016094330 A2 6/2016

OTHER PUBLICATIONS

International Search Report and Written Opinion Dated Aug. 1, 2018 For International Application No. PCT/EP2018/064308 Filed May 18, 20189.
(Continued)

*Primary Examiner* — Reginald R Reyes
(74) *Attorney, Agent, or Firm* — Sherry Austin

(57) ABSTRACT

Various embodiments of the present disclosure are directed to a raw diagnostic machine for a medical diagnosis of raw medical imaging data generated by a medical imaging machine as opposed to a medical diagnosis of a medical image conventionally reconstructed from the raw medical imaging data. In operation, the raw diagnostic engine includes a medical imaging diagnostic controller implementing a dimension reduction pre-processor for selecting or extracting one or more dimension reduced feature vectors from the raw medical imaging data, and further implementing a raw diagnostic artificial intelligence engine for rendering a diagnostic assessment of the raw medical imaging data as represented by the dimension reduced feature vector(s). The medical imaging diagnostic controller may further control a communication of the diagnostic assess-
(Continued)

ment of the raw medical imaging data (e.g., a display, a printing, an emailing, a texting, etc.).

10 Claims, 15 Drawing Sheets

(51) Int. Cl.
    *G06T 11/00*     (2006.01)
    *G16H 30/40*     (2018.01)
    *G16H 50/20*     (2018.01)

(56) References Cited

U.S. PATENT DOCUMENTS

| | | | |
|---|---|---|---|
| 9,373,159 | B2 | 6/2016 | Amroabadi |
| 2008/0080768 | A1 | 4/2008 | Li |
| 2010/0149315 | A1 | 6/2010 | Qu |
| 2015/0042677 | A1* | 2/2015 | Shimamura ......... A61B 6/4233 345/632 |
| 2016/0019320 | A1 | 1/2016 | Kim |
| 2016/0022238 | A1 | 1/2016 | Park |
| 2016/0259898 | A1 | 9/2016 | Young et al. |
| 2016/0284086 | A1* | 9/2016 | Guo ..................... G06T 7/187 |
| 2017/0100078 | A1 | 4/2017 | Han |
| 2019/0066020 | A1* | 2/2019 | Allen .................. G06F 16/285 |
| 2021/0106288 | A1* | 4/2021 | Howard ................ G16H 70/60 |

OTHER PUBLICATIONS

Kohler, et al: "Artifact analysis of approximate helical cone-beam CT reconstruction algorithms", Med. Phys., 2002, 29, 51-64.
https://developer.nvidia.com/clara-medical-imaging.
Guberman: "On Complex Valued Convolutional Neural Networks" (2016). https://arxiv.org/pdf/1602.09046.pdf.
Tramer, et al: "Stealing Machine Learning Models via Prediction APIs", USENIX Security Symposium, 2016.
Razifar et al: "Application of Multivariate Image Analysis in Nuclear Medicine:Principal Component Analysis (PCA) on Dynamic Human Brain Studies With Positron Emission Tomography (PET) for Discrimination of Areas of Disease at High Noise Levels"; Techniques and Applications of Hyperspectral Image Analysis, Edited By H.G. Grahn and P. Geladi, John Wiley & Sons, Ltd, 2007, pp. 313-334.

* cited by examiner

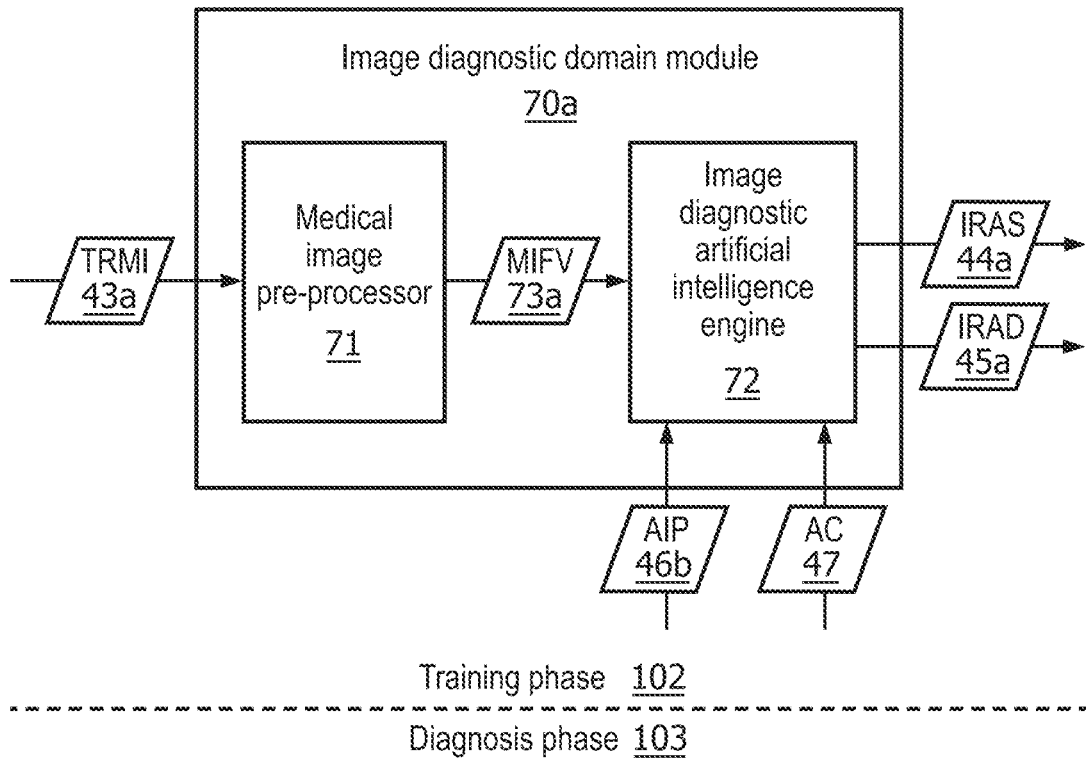
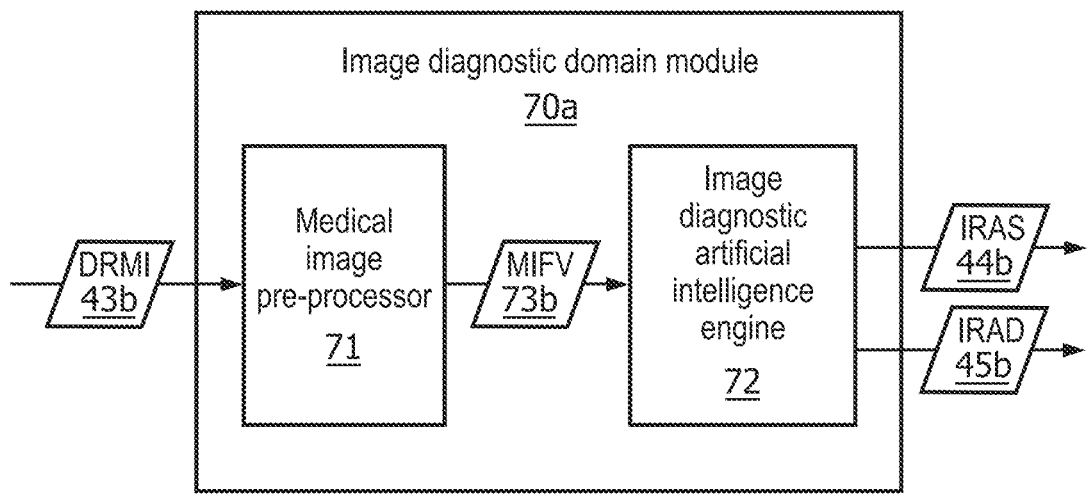
FIG. 8B

| Raw diagnostic domain module 50b (CT: Liver) | Raw diagnostic domain module 50c (CT: Brain) | Raw diagnostic domain module 50d (CT: Thoracic) | Raw diagnostic domain module 50e (CT: Cranial) |
| --- | --- | --- | --- |
| Raw diagnostic domain module 50f (MRI: Lungs) | Raw diagnostic domain module 50g (MRI: Prostate) | Raw diagnostic domain module 50h (MRI: Mammary) | Raw diagnostic domain module 50i (MRI: Sternum) |
| Raw diagnostic domain module 50j (X-Ray: Liver) | Raw diagnostic domain module 50k (X-Ray: Brain) | Raw diagnostic domain module 50l (X-Ray: Thoracic) | Raw diagnostic domain module 50m (X-Ray: Cranial) |
| Raw diagnostic domain module 50n (US: Lungs) | Raw diagnostic domain module 50o (US: Prostate) | Raw diagnostic domain module 50p (US: Mammary) | Raw diagnostic domain module 50q (US: Sternum) |

FIG. 9

MACHINE LEARNING ON RAW MEDICAL IMAGING DATA FOR CLINICAL DECISION SUPPORT

CROSS REFERENCE TO RELATED APPLICATIONS

This application is the U.S. National Phase application under 35 U.S.C. § 371 of International Application No. PCT/EP2018/064308 filed May 30, 2018, published as WO 2018/220089 on Dec. 6, 2018, which claims the benefit of U.S. Provisional Patent Application No. 62/512,774 filed May 31, 2017. These applications are hereby incorporated by reference herein.

TECHNICAL FIELD

Various embodiments described in the present disclosure relate to systems, controllers and methods incorporating artificial intelligence for rendering a diagnostic assessment of a medical imaging of an anatomical region or an anatomical organ, particularly within a domain of raw medical imaging data.

BACKGROUND

Medical imaging data is frequently acquired and subsequently manipulated for human interpretation. For example, computed tomography (CT) medical imaging of an anatomical region or an anatomical organ involves an acquisition of medical imaging data in the form of projection sinogram(s) that is(are) processed to reconstruct a medical image of an anatomical region/organ for human interpretation during a clinical diagnosis of the anatomical region/organ as known in the art of the present disclosure. By further example, magnetic resonance imaging (MRI) of an anatomical region/organ involves an acquisition of medical imaging data in k-space that is processed to reconstruct a medical image of an anatomical region/organ for human interpretation during a clinical diagnosis of the anatomical region/organ as known in the art of the present disclosure.

While the reconstruction of the raw medical imaging data into a medical image for human interpretation during a clinical diagnosis of the anatomical region/organ has proven to support reliable clinical decisions, the image reconstruction process may involve substantial computation time which may result in an inability for a clinician to timely response to an aliment/injury/trauma/damage to the anatomical region/organ requiring immediate attention.

For example, FIG. 1A illustrates a time period 20a of ninety-seven (97) seconds for four (4) Testa 8-series graphical processing units (GPUs) to execute an image reconstruction of raw medical image data generated by a magnetic resonance imaging (MRI) machine, and a time period 20b of 23.2 minutes for a 2.66 GHz Quad-core Intel Core 2 Extreme (CPU) to execute an image reconstruction of the raw MRI data. By further example, FIG. 1B illustrates a time period 21a of 59.9 seconds for four (4) Testa 10-series graphical processing units (GPUs) to execute an image reconstruction of raw medical image data generated by a computed tomography (CT) machine, and a time period 21b of 67.4 seconds for 256 AMD dual-core Opteron 250 central processing units (CPUs) to execute an image reconstruction of the raw CT data. Such computation time as shown in FIGS. 1A and 1B, may result in an inability for a clinician to timely response to an injury/trauma/damage to the anatomical region/organ requiring immediate attention, particularly injury/trauma/damage to the brain.

Furthermore, the image reconstruction process may introduce artifacts into the reconstructed medical image resulting in a less reliable clinical decision (e.g., streaks from metal in a CT imaging, a truncation artefact (gibbs ringing), zipper interference (rf interference) and ghosting).

For example, FIG. 2 illustrates a typical medical image 22 of an ankle at 16 KHz and an ideal medical image 23 of the same ankle at 32 KHz. Medical image 22 includes a chemical shift artefact not present in medical image 23 as would be appreciated by those having skill in the art of the present disclosure.

Additionally, the image reconstruction process may involve a display of a medical image of a smaller range than the complete information range of the medical image. For example, an ultrasound medical imaging involves signal amplitude attenuation with depth and the current technological state of displays/monitors offer a less than full dynamic range of an ultrasound medical image.

For example, FIG. 3 illustrates a display 24 of an ultrasound image of a smaller range than the complete information range 25 of the ultrasound image.

Improvements in algorithms for image reconstruction are being pursued to address the aforementioned computation time, artifact and dynamic display range limitations. Generally, an image reconstruction algorithm may be classified as either a direct image reconstruction algorithm or an iterative image reconstruction algorithm. More particularly, direct image reconstructions are used in almost all of today's medical CT scanners. While such algorithms are fast to compute, they are susceptible to artifacts and noise. Conversely, iterative reconstruction algorithms offer greater accuracy, but at an expense of high computational cost.

SUMMARY

Rather than pursuing a development of a tailored image reconstruction algorithm to minimize the inaccurate effect of image artifacts on a medical diagnosis within a reduced diagnosis computation time, the inventors of the inventions described in the present disclosure discovered, counter-intuitive to the ideology of those having ordinary skill in the art of the present disclosure, that performing a medical diagnosis on raw medical imaging data in its original state of acquisition based on artificial intelligence offers numerous advantages, such as, for example, an elimination of the inaccurate effect of image artifacts on a medical diagnosis and a minimization of diagnosis computation time. More particularly, it is a historically established principle by those having ordinary skill in the art that an evaluation of a medical image of an anatomical region or an anatomical organ is the only means for properly diagnosing a health state of the anatomical region/organ. The inventions of the present disclosure counter this historically established principle by proving an evaluation of the raw medical imaging data, upon which medical images are reconstructed, is a valid alternative means for properly diagnosing a health state of the anatomical region/organ, particularly in time-critical emergencies.

One embodiment of the inventions of the present disclosure is a medical imaging diagnostic system employing a medical imaging machine for generating raw medical imaging data, and a raw diagnostic machine for a medical diagnosis of the raw medical imaging data generated by the medical imaging machine. The raw diagnostic machine includes a medical imaging diagnostic controller configured to (1) input the raw medical imaging data into a dimension reduction pre-processor trained to select or extract one or more dimension reduced feature vector(s) from the raw medical imaging data, (2) input the dimension reduced feature vector(s) into a raw diagnostic artificial intelligence engine (e.g., an artificial neural network and/or a supervised learning machine) trained to render a diagnostic assessment of the raw medical imaging data, and (3) control a communication of the diagnostic assessment of the raw medical imaging data (e.g., a display, a printing, an emailing, a texting, etc. of the diagnostic assessment of the raw medical imaging data).

The medical imaging diagnostic controller may be further configured to (4) input the raw medical imaging data into a medical image reconstruction engine to generate a reconstructed medical image and (5) communicate the reconstructed medical image (e.g., a display, a printing, an emailing, a texting, etc. of the reconstructed medical image).

The medical imaging diagnostic controller may be further configured to (6) input a reconstructed medical image into a medical image pre-processor trained to select or extract one or more medical image feature vector(s) from the reconstructed medical image, (7) input the medical image feature vector(s) into an image diagnostic artificial intelligence engine trained to render a diagnostic assessment of the reconstructed medical image, and (8) communicate the reconstructed medical image (e.g., a display, a printing, an emailing, a texting, etc. of the medical image of the reconstructed medical image).

A second embodiment of the inventions of the present disclosure is a non-transitory machine-readable storage medium encoded with instructions for execution by at least one processor for processing raw medical imaging data generated by a medical imaging machine. The non-transitory machine-readable storage medium comprises instructions to (1) input the raw medical imaging data into a dimension reduction pre-processor trained to select or extract one or more dimension reduced feature vector(s) from the raw medical imaging data, and (2) input the dimension reduced feature vector(s) into a raw diagnostic artificial intelligence engine (e.g., an artificial neural network and/or a supervised learning machine) trained to render a diagnostic assessment of the raw medical imaging data.

The non-transitory machine-readable storage medium may further comprise instructions to (3) input the raw medical imaging data into a medical image reconstruction engine to generate a reconstructed medical image.

The non-transitory machine-readable storage medium may further comprise instructions to (4) input a reconstructed medical image into a medical image pre-processor trained to select or extract one or more medical image feature vector(s) from the reconstructed medical image and (5) input the medical image feature vector(s) into an image diagnostic artificial intelligence engine trained to render a diagnostic assessment of the reconstructed medical image.

A third embodiment of the inventions of the present disclosure is a medical imaging diagnostic method for a medical diagnosis by a medical imaging diagnostic controller of raw medical imaging data generated by a medical imaging machine. The medical imaging diagnostic method involves (1) an inputting, by the medical imaging diagnostic controller, of the raw medical imaging data into a dimension reduction pre-processor trained to select or extract one or more dimension reduced feature vectors from the raw medical imaging data, and (2) an inputting, by the medical imaging diagnostic controller, of the dimension reduced feature vector(s) into a raw diagnostic artificial intelligence engine (e.g., an artificial neural network and/or a supervised learning machine) to render a diagnostic assessment of the raw medical imaging data.

The medical imaging diagnostic method may further involve (3) an inputting, by the medical imaging diagnostic controller, of raw medical imaging data into a medical image reconstruction engine to generate a reconstructed medical image.

The non-transitory machine-readable storage medium may further comprise instructions to (4) an inputting, by the medical imaging diagnostic controller, of a reconstructed medical image into a medical image pre-processor trained to select or extract one or more medical image feature vector(s) from the reconstructed medical image and (5) an inputting, by the medical imaging diagnostic controller, of the medical image feature vector(s) into an image diagnostic artificial intelligence engine trained to render a diagnostic assessment of the reconstructed medical image.

For purposes of describing and claiming the inventions of the present disclosure:

(1) the terms of the art of the present disclosure including, but not limited to, "artificial intelligence", "feature vector", "artificial neural network", "supervised learning machine", "dimension reduction", "image reconstruction", "anatomical region" and "anatomical organ" are to be broadly interpreted as known in the art of the present disclosure and exemplary described in the present disclosure;

(2) the term "medical imaging machine" broadly encompasses any imaging modality, as understood in the art of the present disclosure and hereinafter conceived, for executing a diagnostic imaging of an anatomical region or an anatomical organ. Examples of a medical imaging machine include, but are not limited to, an X-ray machine, an ultrasound machine, a computed tomography (CT) machine, a magnetic resonance imaging (MRI) machine, a positron emission tomography (PET) machine, a single photon emission computed tomography (SPECT) machine and a diffuse optical tomography (DOT) machine;

(3) the term "raw medical imaging data" broadly encompasses electronic data acquired by a medical imaging machine as understood in the art of the present disclosure and hereinafter conceived. Examples of raw medical imaging data include, but are not limited to, MRI in k-space, CT sinograms, raw ultrasound data and PET listmode files;

(4) the term "raw diagnostic machine" broadly encompasses any machine configured in accordance with the inventive principles of the present disclosure for an artificial intelligence based medical diagnosis of raw medical imaging data as exemplarily described in the present disclosure;

(5) the term "controller" broadly encompasses all structural configurations, as understood in the art of the present disclosure and hereinafter conceived, of an application specific main board or an application specific integrated circuit for controlling an application of various inventive principles of the present disclosure as subsequently described in the present disclosure. The structural configuration of the controller may include, but is not limited to, processor(s), non-transitory machine-readable storage medium(s), an operating system, application module(s), peripheral device controller(s), slot(s) and port(s);

(6) the term "module" broadly encompasses electronic circuitry/hardware and/or an executable program (e.g., executable software stored on non-transitory computer readable medium(s) and/or firmware) incorporated within or accessible by a controller for executing a specific application;

(7) the descriptive labels for term "module" herein facilitates a distinction between modules as described and claimed herein without specifying or implying any additional limitation to the term "module";

(8) the term "dimension reduction pre-processor" broadly encompasses any type of data prep-processor, as understood in the art of the present disclosure and hereinafter conceived, configured in accordance with the inventive principles of the present disclosure to implement a dimension reduction technique of feature selection (e.g., a filtering, a wrapping or an embedded evaluation) or feature extraction (e.g., a principle component analysis or a linear discriminant analysis) of raw medical imaging data;

(9) the term "dimension reduced feature vector" broadly encompasses a feature vector selected or extracted from raw medical imaging data by a dimension reduction pre-processor that is representative of classifying/predictive features of the raw medical imaging data;

(9) the term "raw diagnostic artificial intelligence engine" broadly encompasses any type of artificial intelligence engine, as understood in the art of the present disclosure and hereinafter conceived, configured in accordance with the inventive principles of the present disclosure to implement an identification, a classification or a prediction of a medical diagnosis of raw medical imaging data as exemplarily described in the present disclosure. Examples of a raw diagnostic artificial intelligence engine include, but are not limited to, an artificial neural network (e.g., convolutional neural network, a recurrent neural network, etc.) and a supervised learning machine (e.g., a support vector machine);

(10) the term "medical image reconstruction engine" broadly encompasses any type of computing engine, as understood in the art of the present disclosure and hereinafter conceived, to implement an image reconstruction of raw medical imaging data to thereby generate a reconstructed medical image;

(11) the term "image construction pre-processor" broadly encompasses any type of data prep-processor, as understood in the art of the present disclosure and herein after conceived, configured in accordance with the inventive principles of the present disclosure to implement a feature extraction technique of a reconstructed medical image;

(12) the term "medical image feature vector" broadly encompasses a feature vector extracted from a reconstructed medial image by an image reconstruction pre-processor that is representative of classifying/predictive features of the reconstructed medial image; and

(13) "data" may be embodied in all forms of a detectable physical quantity or impulse (e.g., voltage, current, magnetic field strength, impedance, color) as understood in the art of the present disclosure and as exemplary described in the present disclosure for transmitting information and/or instructions in support of applying various inventive principles of the present disclosure as subsequently described in the present disclosure. Data communication encompassed by the inventions of the present disclosure may involve any communication method as known in the art of the present disclosure including, but not limited to, data transmission/reception over any type of wired or wireless datalink and a reading of data uploaded to a computer-usable/computer readable storage medium.

The foregoing embodiments and other embodiments of the inventions of the present disclosure as well as various features and advantages of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of present disclosure being defined by the appended claims and equivalents thereof.

BRIEF DESCRIPTION OF THE DRAWINGS

In order to better understand various example embodiments, reference is made to the accompanying drawings, wherein:

FIG. 8B illustrates an exemplary training phase and an exemplary diagnostic phase of an image diagnostic domain module in accordance with the inventive principles of the present disclosure;

FIG. 9 illustrates exemplary embodiments of a raw diagnostic domain module in accordance with the inventive principles of the present disclosure;

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described in the present disclosure are not necessarily mutually exclusive and may be combined to produce additional embodiments that incorporate the principles described in the present disclosure.

As will be further explained in detail in the present disclosure, the inventions of the present disclosure are premised on a dimension reduction of raw medical imaging data to thereby facilitate an identification, a classification or a prediction by an artificial intelligence engine of a particular medical diagnosis of the raw medical imaging data. More particularly, the dimensions reduction provides viable variables of the raw medical imaging data that enables the artificial intelligence engine to identify, classify or predict a particular medical diagnosis of an anatomical region or an anatomical organ corresponding to the raw medical imaging data among a range of medical diagnoses between a healthy state (e.g., an identification, a classification or a prediction of an absence of an aliment/injury/trauma/damage in/to the anatomical region/organ) and an unhealthy state (e.g., an identification, a classification or a prediction of a presence aliment/injury/trauma/damage in/to the anatomical region/organ).

Figure 1A:
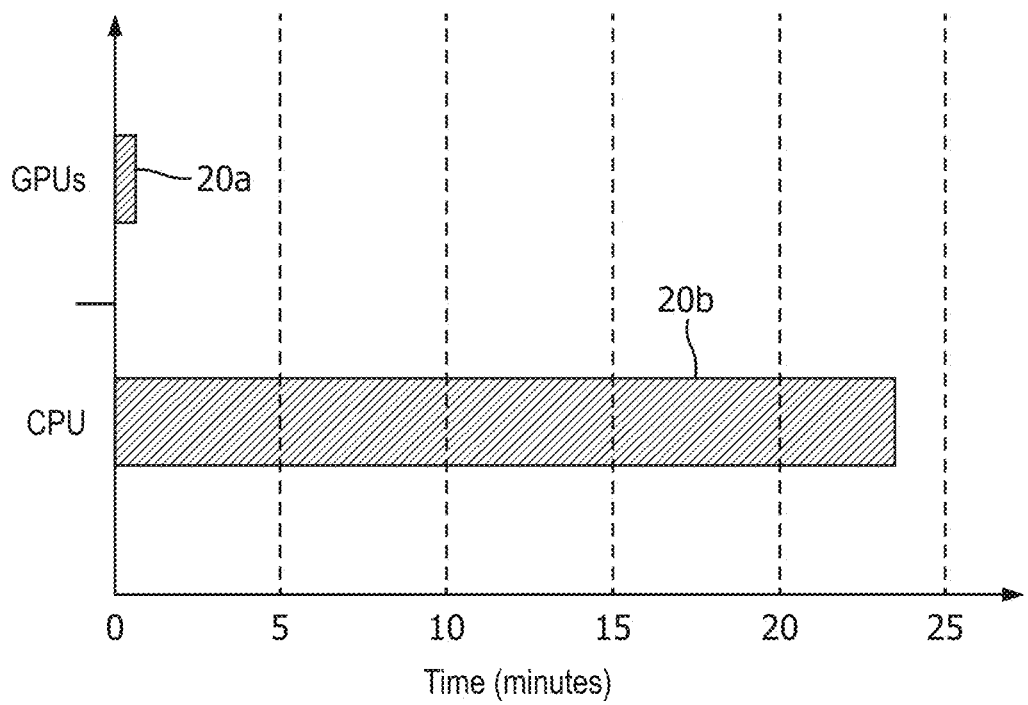
FIG. 1A illustrates exemplary reconstruction times for an advanced MRI as known in the art of the present disclosure.
Figure 1B:
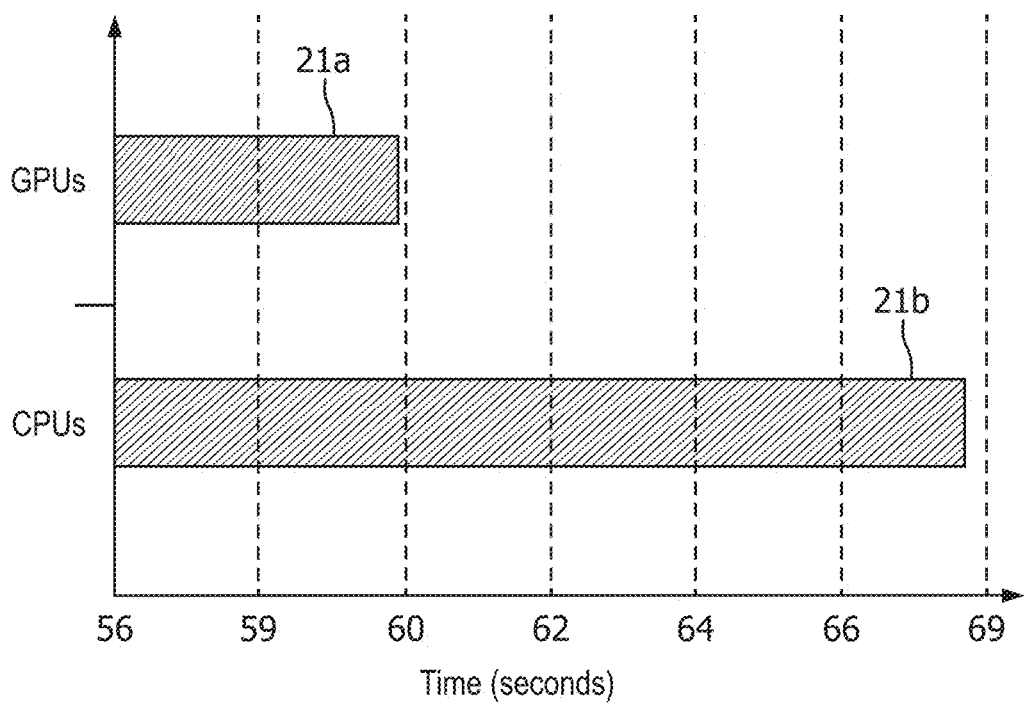
FIG. 1B illustrates exemplary reconstruction times for CT imaging as known in the art of the present disclosure.
Figure 2:
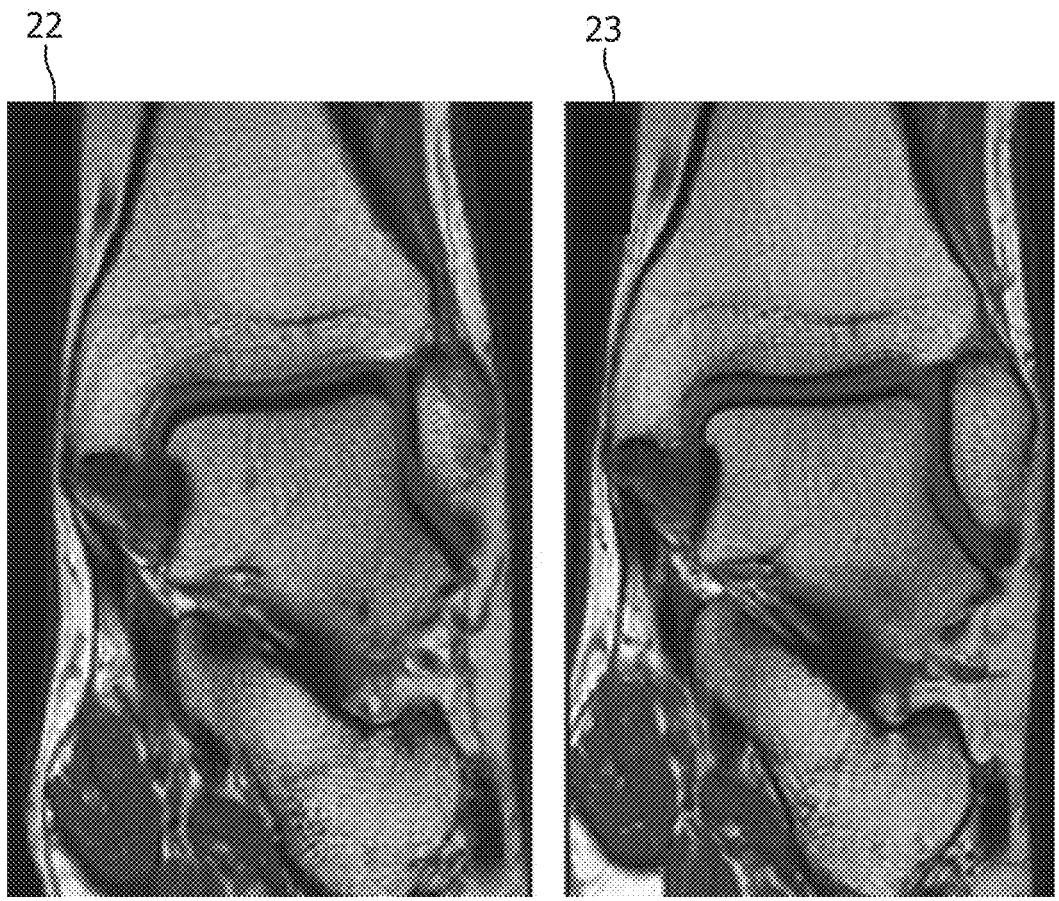
FIG. 2 illustrates exemplary imaging of an ankle as known in the art of the present disclosure.
Figure 3:
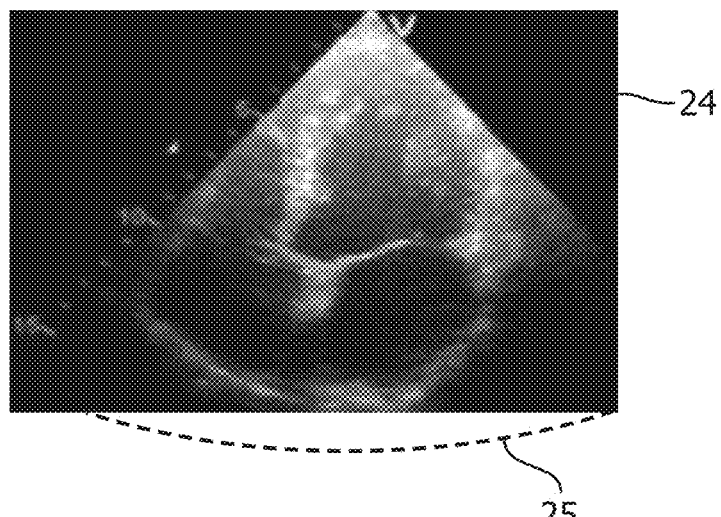
FIG. 3 illustrates exemplary ultrasound image as known in the art of the present disclosure.
Figure 4A:
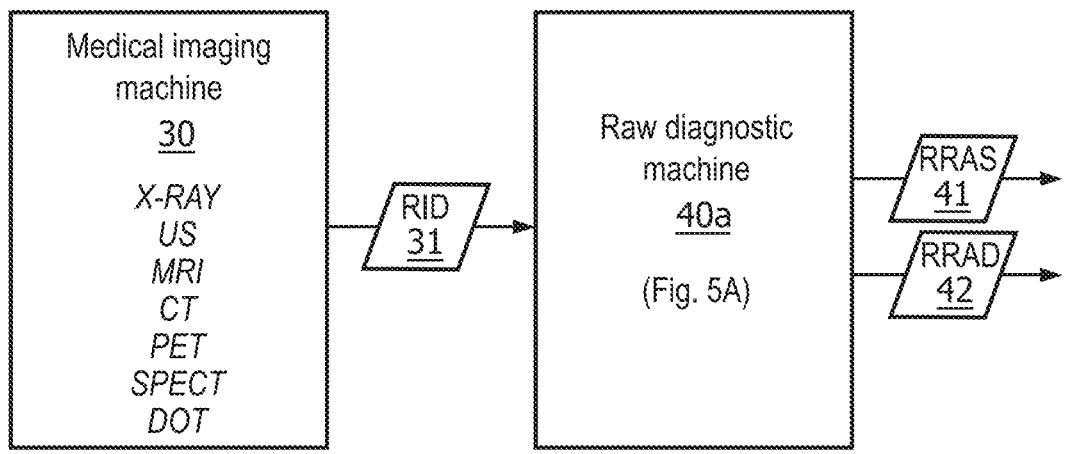
FIGS. 4A-4C illustrate exemplary embodiments of a medical imaging diagnostic system in accordance with the inventive principles of the present disclosure.
Figure 4B:
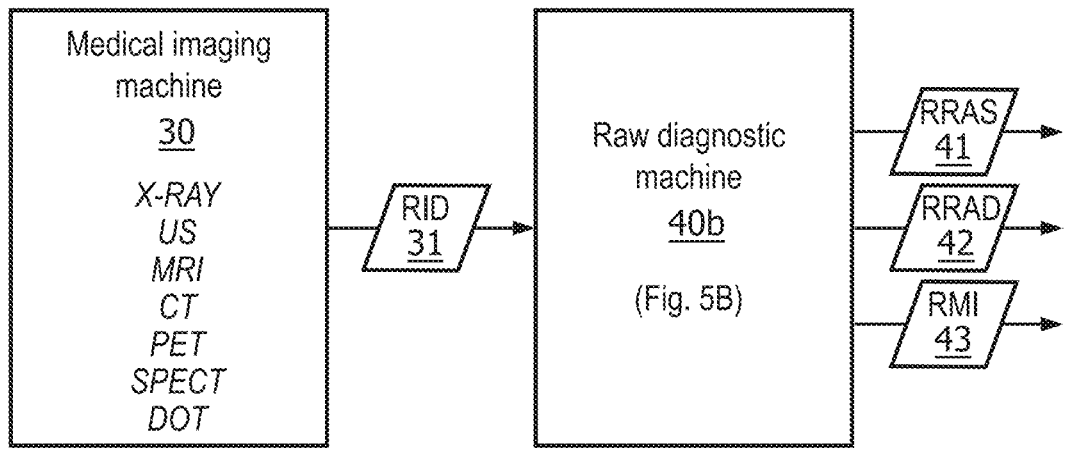
Figure 4C:
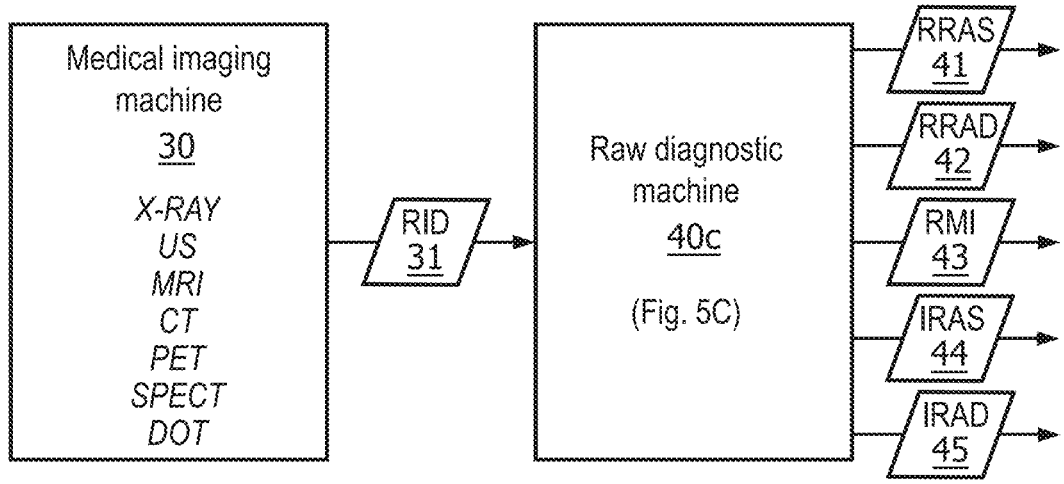

To facilitate an understanding of the inventions of the present disclosure, the following description of FIGS. 4A-4C teach various embodiments of a medical imaging diagnostic system of the present disclosure. From the description of FIGS. 4A-4C, those having ordinary skill in the art of the present disclosure will appreciate how to apply the present disclosure for making and using numerous and various additional embodiments of medical imaging diagnostic systems of the present disclosure.

FIG. 4A illustrates one embodiment of a medical imaging diagnostic system of the present disclosure employing a medical imaging machine 30 as known in the art of the present disclosure and a raw diagnostic machine 40a in accordance with the inventive principles of the present disclosure.

Referring to FIG. 4A, in practice, medical imaging machine 30 acquires raw imaging data 31 of an anatomical region or an anatomical organ as known in the art of the present disclosure, particularly for X-ray machines, ultrasound machines, MRI machines, CT machines, PET machines, SPECT machines and DOT machines.

Still referring to FIG. 4A, raw diagnostic machine 40a processes raw medical imaging data 31, as will be further explained in the present disclosure, to render a diagnostic assessment of the raw medical imaging data 31. In practice, raw diagnostic machine 40a will have a structural architecture trained for inputting and processing raw medical imaging data 31 from one or more types of medical imaging machine 30, and/or for processing raw medical imaging data 31 corresponding to one or more anatomical regions and/or anatomical organs.

Also in practice, the diagnostic assessment may be in any form that communicates an identification, a classification or a prediction a particular medical diagnosis of the raw medical imaging data 31. In one embodiment as shown, raw diagnostic machine 40a outputs a raw risk assessment score 41 whereby a level of the score 41 is indictive of an identification, a classification or a prediction a particular medical diagnosis of the raw medical imaging data 31. For example, on a scale of zero (0) to one (1), a zero (0) level indicates an identification, a classification or a prediction of an absence of an aliment/injury/trauma/damage in/to the anatomical region/organ and a one (1) level a classification or a prediction of a presence of an aliment/injury/trauma/damage in/to the anatomical region/organ. Additionally, intermediate levels between zero (0) and one (1) may be used to indicate a degree of uncertainty/certainty of a prediction of a presence of an aliment/injury/trauma/damage in/to the anatomical region/organ. Raw diagnostic machine 40a may further output a raw risk assessment description 42 of the an identification, a classification or a prediction of a particular medical diagnosis of the raw medical imaging data 31.

FIG. 4B illustrates a second embodiment of a medical imaging diagnostic system of the present disclosure employing medical imaging machine 30 as known in the art of the present disclosure and a raw diagnostic machine 40b in accordance with the inventive principles of the present disclosure.

Referring to FIG. 4B, in practice, medical imaging machine 30 acquires raw imaging data 31 of an anatomical region or an anatomical organ as known in the art of the present disclosure and previously described for FIG. 4A.

Still referring to FIG. 4B, raw diagnostic machine 40b processes raw medical imaging data 31, as will be further explained in the present disclosure, to render a diagnostic assessment of the raw medical imaging data 31 as previously described for raw diagnostic machine 40a (FIG. 4A). In addition thereto, raw diagnostic machine 40b executes an image reconstruction technique as known the art for generating a reconstructed medical image 43 corresponding to the particular type of raw medical imaging data 31 acquired from medical imaging machine 30 (e.g., an X-ray image from the raw medical imaging data 31 acquired from an X-ray machine, an ultrasound image from the raw medical imaging data 31 acquired from an X-ray machine, etc.).

FIG. 4C illustrates a third embodiment of a medical imaging diagnostic system of the present disclosure employing medical imaging machine 30 as known in the art of the present disclosure and a raw diagnostic machine 40c in accordance with the inventive principles of the present disclosure.

Referring to FIG. 4C, in practice, medical imaging machine 30 acquires raw imaging data 31 of an anatomical region or an anatomical organ as known in the art of the present disclosure and previously described for FIG. 4A.

Still referring to FIG. 4C, raw diagnostic machine 40c processes raw medical imaging data 31, as will be further explained in the present disclosure, to render a diagnostic assessment of the raw medical imaging data 31 and to reconstruct a medial image as previously described for raw diagnostic machine 40b (FIG. 4B).

In addition thereto, raw diagnostic machine 40c processes raw medical imaging data 31, as will be further explained in the present disclosure, to render a diagnostic assessment of the reconstructed medical image 43. In practice, the diagnostic assessment may be in any form that communicates an identification, a classification or a prediction a particular medical diagnosis of the reconstructed medical image 43. In one embodiment as shown, raw diagnostic machine 40c outputs an image risk assessment score 41 whereby a level of the score 44 is indictive of an identification, a classification or a prediction a particular medical diagnosis of the reconstructed medical image 43. Again, for example, on a scale of zero (0) to one (1), a zero (0) level indicates an identification, a classification or a prediction of an absence of an aliment/injury/trauma/damage in/to the anatomical region/organ and a one (1) level a classification or a prediction of a presence of an aliment/injury/trauma/damage in/to the anatomical region/organ. Additionally, intermediate levels between zero (0) and one (1) may be used to indicate a degree of uncertainty/certainty of a prediction of a presence of an aliment/injury/trauma/damage in/to the anatomical region/organ. Raw diagnostic machine 40b may further output a raw risk assessment description 45 of the an identification, a classification or a prediction of a particular medical diagnosis of the reconstructed medical image 43.

Figure 5A:
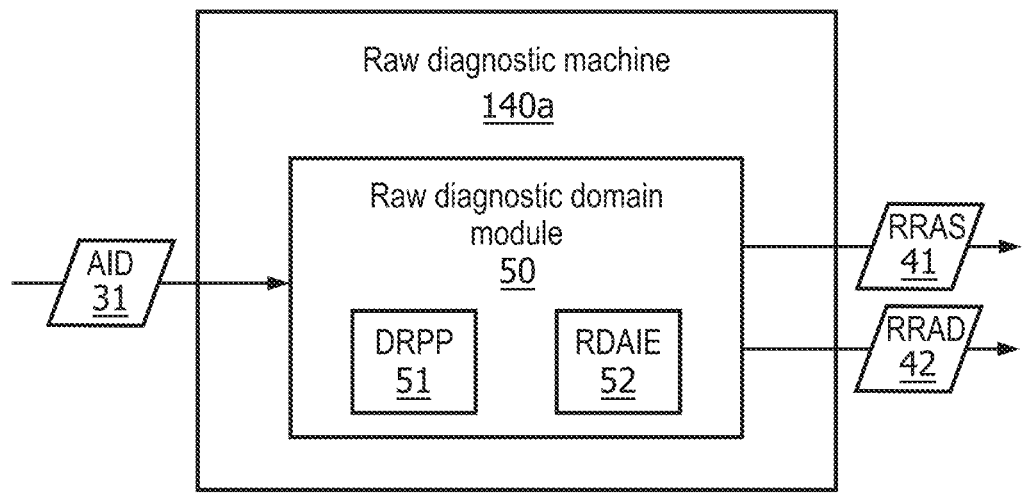
FIGS. 5A-5C illustrate exemplary embodiments of a raw diagnostic machine in accordance with the inventive principles of the present disclosure.
Figure 5B:
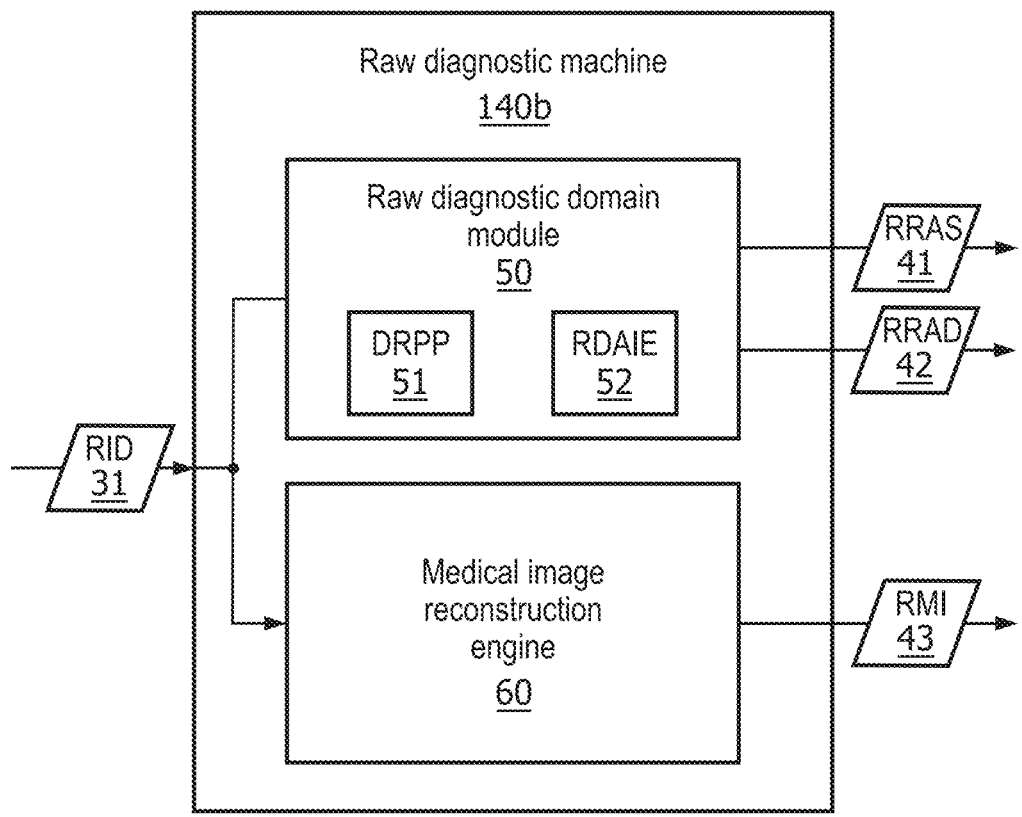
Figure 5C:
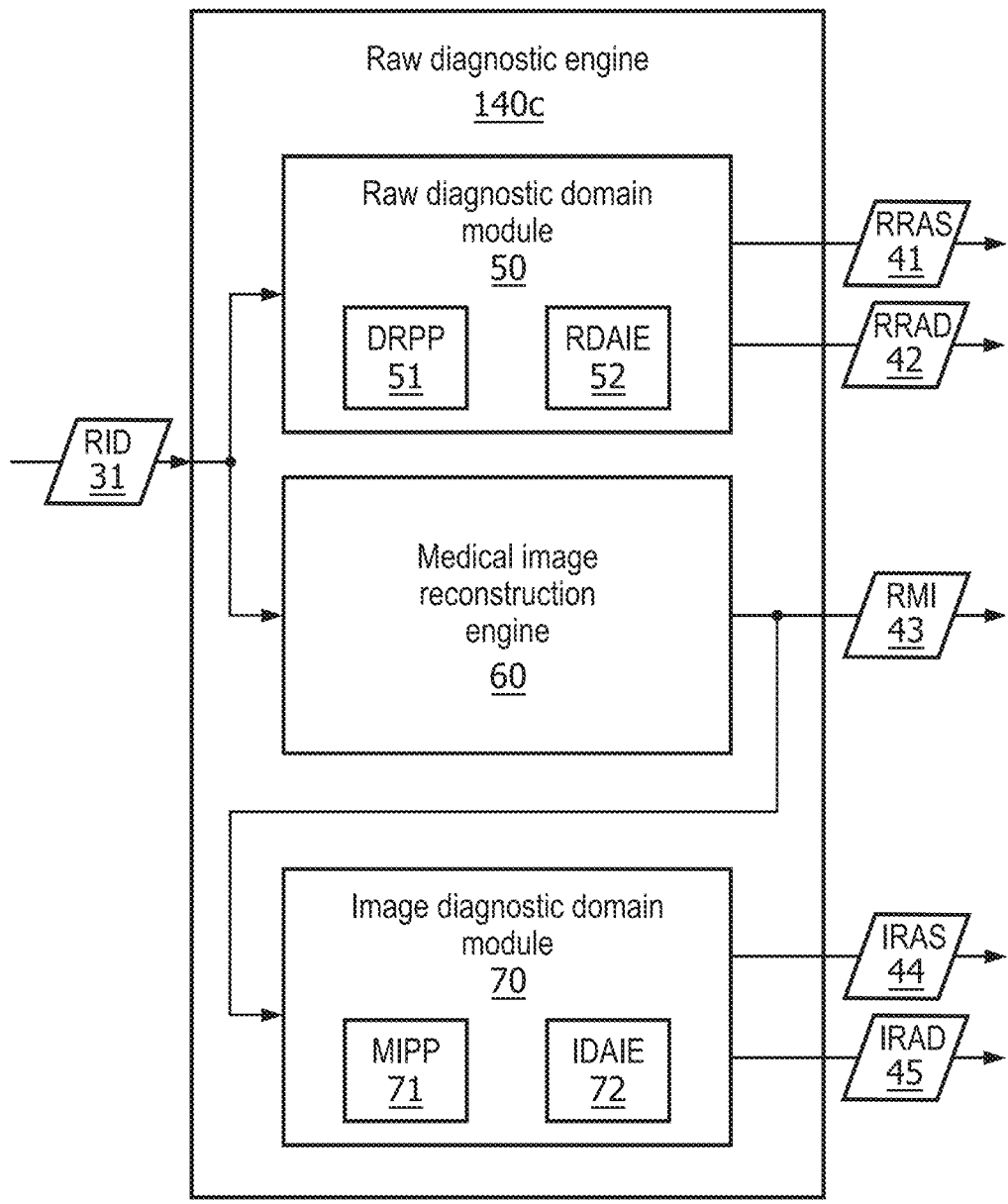

To further facilitate an understanding of the inventions of the present disclosure, the following description of FIGS. 5A-5C teach various embodiments of a raw diagnostic machine of the present disclosure. From the description of FIGS. 5A-5C, those having ordinary skill in the art of the present disclosure will appreciate how to apply the present disclosure for making and using numerous and various additional embodiments of raw diagnostic machines of the present disclosure.

FIG. 5A illustrates an embodiment 140a of raw diagnostic machine 40a (FIG. 4A). Referring to FIG. 5A, raw diagnostic machine 140a includes a raw diagnostic domain module 50 employing a dimension reduction pre-processor 51 and a raw diagnostic artificial intelligence engine 52.

In practice, dimension reduction pre-processor 51 is a data pre-processor configured in accordance with the inventive principles of the present disclosure to reduce the number of random variables of raw medical imaging data 31 into a set of principle variables to thereby acquire a dimension reduced feature vector as will be further explained in the present disclosure.

In one embodiment, dimension reduction pre-processor 51 implements a dimension reduction technique of feature selection (e.g., a filtering, a wrapping or an embedded evaluation) to reduce the number of random variables of raw medical imaging data 31 into a set of principle variables to thereby select the dimension reduced feature vector.

In a second embodiment, dimension reduction pre-processor 51 implements a dimension reduction technique of feature extraction (e.g., a principle component analysis or a linear discriminant analysis) to reduce the number of random variables of raw medical imaging data 31 into a set of principle variables to thereby extract the dimension reduced feature vector.

Still referring to FIG. 5A, in practice, raw diagnostic artificial intelligence engine 52 renders a diagnostic assessment of the raw medical imaging data 31, such as, for example, raw risk assessment score 41 and raw risk assessment description 42 as previously described in the present disclosure (FIG. 4A).

In one embodiment, raw diagnostic artificial intelligence engine 52 includes one or more artificial neural network(s) (e.g., a convolutional neural network, a recurrent neural network, etc.) trained to render the diagnostic assessment of the raw medical imaging data 31 as will be further explained herein.

In a second embodiment, raw diagnostic artificial intelligence engine 52 includes one or more supervised learning machine(s) (e.g., a support vector machine) to trained to render the diagnostic assessment of the raw medical imaging data 31 as will be further explained herein.

FIG. 5B illustrates one embodiment 140b of raw diagnostic machine 40b (FIG. 4B). Referring to FIG. 5B, raw diagnostic machine 140b includes raw diagnostic domain module 50 as previously described in the present disclosure (FIG. 5A). Raw diagnostic machine 140b further includes a medical image reconstruction engine 60 to reconstruct a medical image 43 from raw medical imaging data 31 as known in the art of the present disclosure.

In one embodiment, medical image reconstruction engine 60 implements a direct image reconstruction algorithm as known in the art of the present disclosure.

In a second embodiment, medical image reconstruction engine 60 implements an iterative image reconstruction algorithm as known in the art of the present disclosure.

FIG. 5C illustrates one embodiment 140c of raw diagnostic machine 40c (FIG. 4C). Referring to FIG. 5C, raw diagnostic machine 140C includes raw diagnostic domain module 50 as previously described in the present disclosure (FIG. 5A) and medical image reconstruction engine 60 as previously described in the present disclosure (FIG. 5B). Raw diagnostic machine 140c further includes an image diagnostic domain module 70 employing a medical image pre-processor 71 and an image diagnostic artificial intelligence engine 72.

In practice, medical image pre-processor 71 is a data pre-processor configured as known in the art of the present disclosure for extracting a medical image feature vector from the reconstructed medical image 43 as will be further explained in the present disclosure.

Still referring to FIG. 5B, in practice, image diagnostic artificial intelligence engine 72 renders a diagnostic assessment of the reconstructed medical image 43, such as, for example, image risk assessment score 44 and image risk assessment description 45 as previously described in the present disclosure (FIG. 4C).

In one embodiment, image diagnostic artificial intelligence engine 72 includes one or more artificial neural network(s) (e.g., a convolutional neural network, a recurrent neural network, etc.) trained to render the diagnostic assessment of the reconstructed medical image 43 as will be further explained herein.

In a second embodiment, image diagnostic artificial intelligence engine 72 includes one or more supervised learning machine(s) (e.g., a support vector machine) to trained to render the diagnostic assessment of the reconstructed medical image 43 as will be further explained herein.

Figure 6:
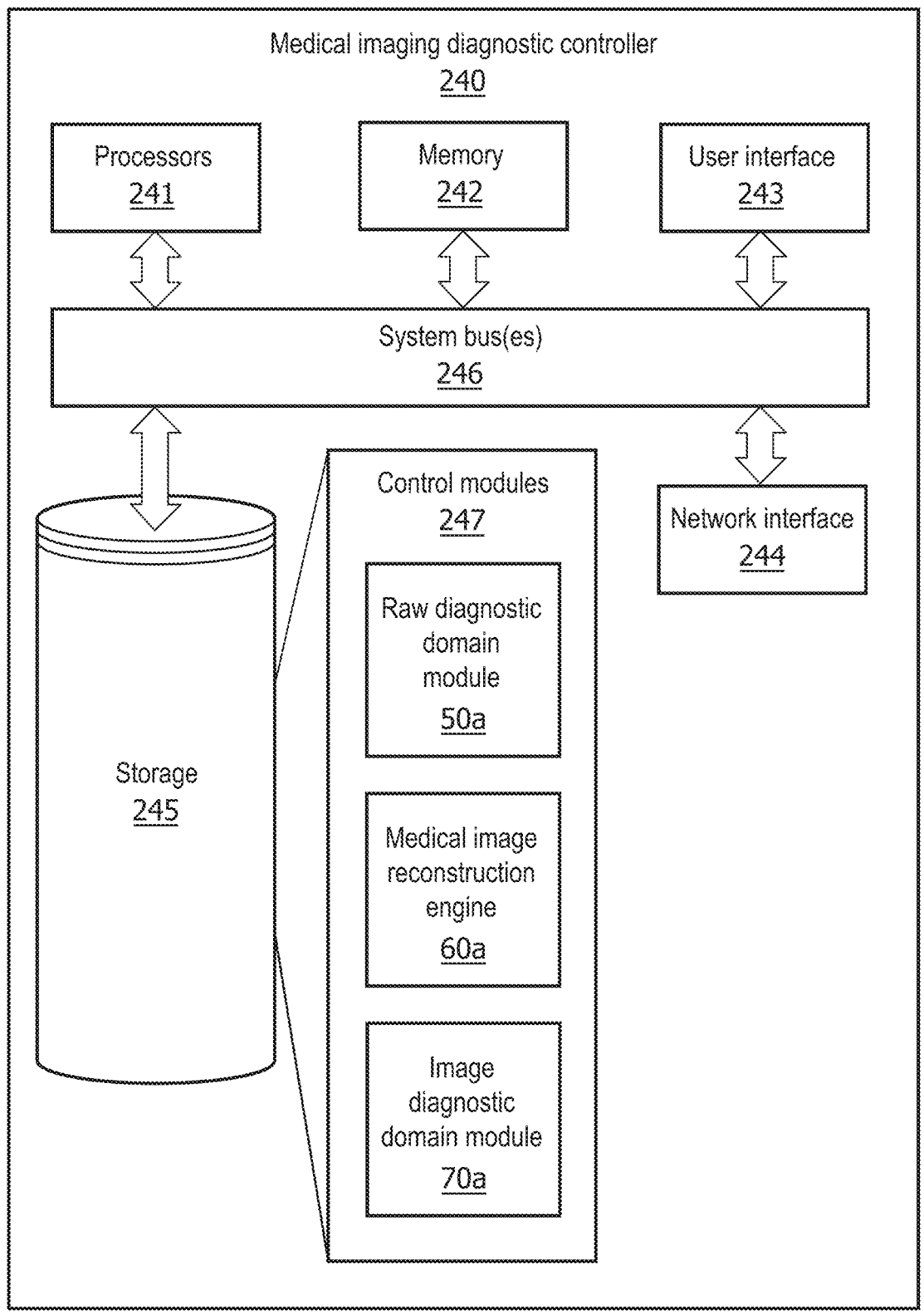
FIG. 6 illustrates an exemplary embodiment of a medical imaging diagnostic controller in accordance with the inventive principles of the present disclosure.
Figure 7:
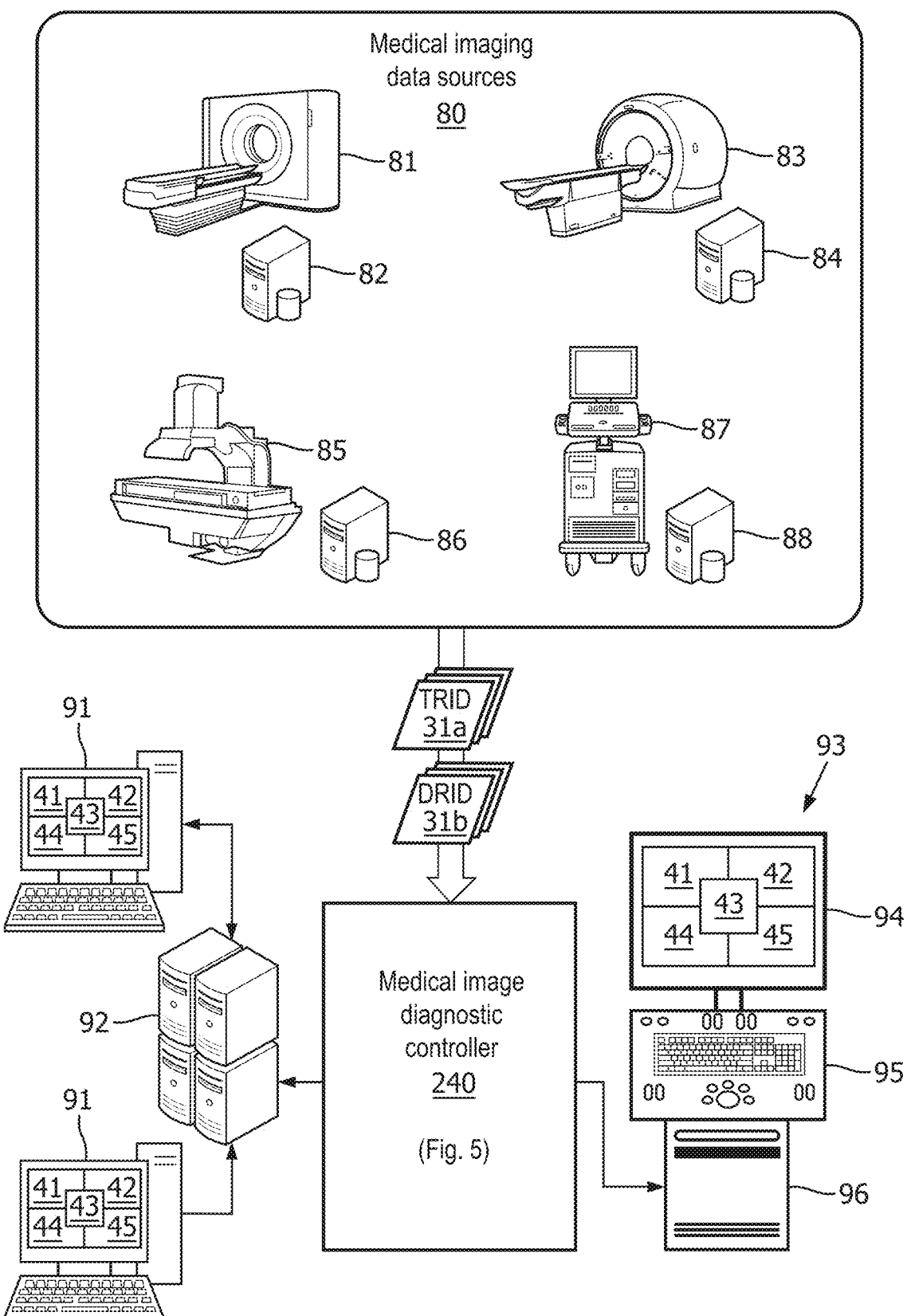
FIG. 7 illustrates exemplary embodiments of a medical imaging diagnostic working configurations in accordance with the inventive principles of the present disclosure.

To further facilitate an understanding of the inventions of the present disclosure, the following description of FIGS. 6 and 7 teach various embodiments of a medical imaging diagnostic controller of the present disclosure. From the description of FIGS. 6 and 7, those having ordinary skill in the art of the present disclosure will appreciate how to apply the present disclosure for making and using numerous and various additional embodiments of medical imaging diagnostic controllers of the present disclosure.

In practice, a medical imaging diagnostic controller of the present disclosure may be implemented as hardware/circuitry/software/firmware for implementing a raw diagnostic machine of the present disclosure, such as, for example, raw diagnostic machine 140a (FIG. 5A), raw diagnostic machine 140b (FIG. 5B) and raw diagnostic machine 140c (FIG. 5C).

In one embodiment as shown in FIG. 6, a medical imaging diagnostic controller 240 includes a processor 241, a memory 242, a user interface 243, a network interface 244, and a storage 245 interconnected via one or more system bus(es) 246. In practice, the actual organization of the components 241-245 of controller 240a may be more complex than illustrated.

The processor 241 may be any hardware device capable of executing instructions stored in memory or storage or otherwise processing data. As such, the processor 241 may include a microprocessor, field programmable gate array (FPGA), application-specific integrated circuit (ASIC), or other similar devices.

The memory 242 may include various memories such as, for example L1, L2, or L3 cache or system memory. As such, the memory 242 may include static random access memory (SRAM), dynamic RAM (DRAM), flash memory, read only memory (ROM), or other similar memory devices.

The user interface 243 may include one or more devices for enabling communication with a user such as an administrator. For example, the user interface 243 may include a display, a mouse, and a keyboard for receiving user commands. In some embodiments, the user interface 243 may include a command line interface or graphical user interface that may be presented to a remote terminal via the network interface 244.

The network interface 244 may include one or more devices for enabling communication with other hardware devices. For example, the network interface 244 may include a network interface card (NIC) configured to communicate according to the Ethernet protocol. Additionally, the network interface 244 may implement a TCP/IP stack for communication according to the TCP/IP protocols. Various alternative or additional hardware or configurations for the network interface will be apparent.

The storage 245 may include one or more machine-readable storage media such as read-only memory (ROM), random-access memory (RAM), magnetic disk storage media, optical storage media, flash-memory devices, or similar storage media. In various embodiments, the storage 245 may store instructions for execution by the processor 241 or data upon with the processor 241 may operate. For example, the storage 245 store a base operating system (not shown) for controlling various basic operations of the hardware.

More particular to the present disclosure, in one embodiment, storage 245 may store a control module 247 in the form of a raw diagnostic domain module 50a as a computer instruction embodiment of raw diagnostic domain module 50 for purposes of implementing raw diagnostic machine 140a (FIG. 5A).

In a second embodiment, storage 245 may store control modules 247 in the form of raw diagnostic domain module 50a as a computer instruction embodiment of raw diagnostic domain module 50 (FIG. 5B) and medical image reconstruction engine 60a as a computer instruction embodiment of medical image reconstruction engine 60a (FIG. 5B) for purposes of implementing raw diagnostic machine 140b (FIG. 5B).

In a third embodiment, storage 245 may store control modules 247 in the form of raw diagnostic domain module 50a as a computer instruction embodiment of raw diagnostic domain module 50 (FIG. 5C), medical image reconstruction engine 60a as a computer instruction embodiment of medical image reconstruction engine 60a (FIG. 5C) and image diagnostic domain module 70a as a computer instruction embodiment of image diagnostic domain module 70 (FIG. 5C) for purposes of implementing raw diagnostic machine 140c (FIG. 5C).

Referring to FIG. 7, in practice, medical image diagnostic controller 240 may be installed within an application server 90 accessible by a plurality of clients (e.g., a client 91 and a client 92 as shown) and/or is installed within a workstation 93 employing a monitor 94, a keyboard 95 and a computer 96.

Figure 8A:
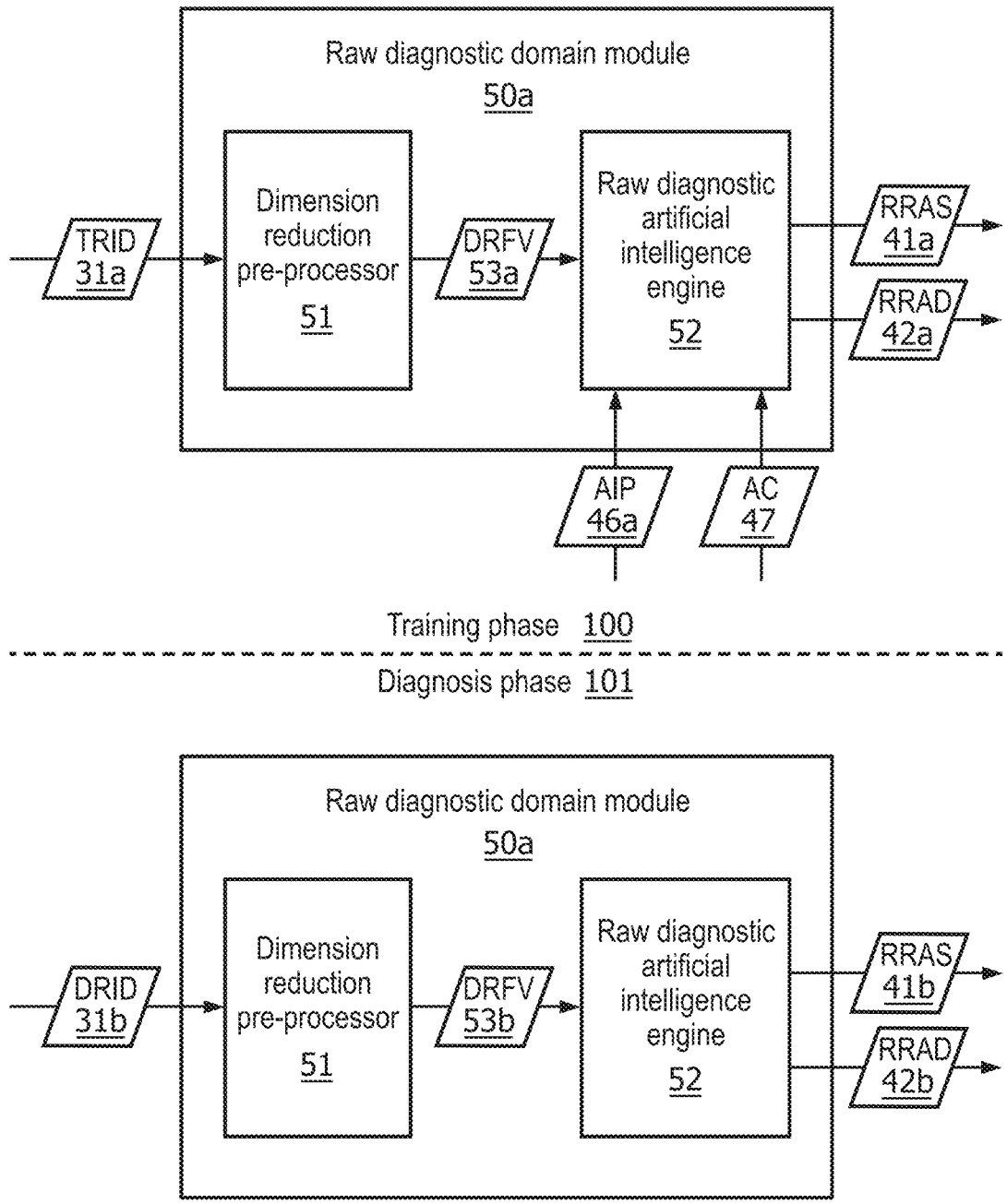
FIG. 8A illustrates an exemplary training phase and an exemplary diagnostic phase of a raw diagnostic domain module in accordance with the inventive principles of the present disclosure.

In operation, medical image diagnostic controller 240 inputs training raw medical imaging data 31a from medical imaging data sources 80 during a training phase as will be further explained in the present disclosure (FIG. 8A) and inputs diagnostic raw medical imaging data 31b as will be further explained in the present disclosure (FIG. 8A). Medical imaging data sources 80 may include any number and types of medical imaging machines (e.g., a MRI machine 81, a CT machine 83, an X-ray machine 85 and an ultrasound machine 87 as shown) and may further includes database management/file servers (e.g., MRI database management server 82, CT server 84, X-ray database management server 86 and ultrasound database manager server 88 as shown). In practice, application server 90 or workstation 93, whichever is applicable, may be directly or networked connected to a medical imaging data source 90 to thereby input the raw medical imaging data 31a/31b for medical image diagnostic controller 240. Alternatively, a medical imaging data source 90 and application server 90 or workstation 93, whichever is applicable, may be directly integrated whereby the medical image diagnostic controller 240 has access to the raw medical imaging data 31a/31b.

Also in practice, application server 90 or workstation 93, whichever is applicable, further includes a display controller as known in the art of the present disclosure for facilitating a communication of the diagnostic assessment of raw medical imaging data 31a/31b to an operator of clients 91/92 or workstation 93, such as, for example, a display of raw risk assessment score 41 (e.g., a textual and/or color-coded display), raw risk assessment description 42, reconstructed medical image 43 (e.g., two-dimensional and/or three-dimensional images), image risk assessment score 44 (e.g., a textual and/or color-coded display) and image risk assessment description 45 as shown. Application server 90 or workstation 93, whichever is applicable, may include other controllers as known in the art of the present disclosure for other forms of communication of the diagnostic assessment of raw medical imaging data 31a/31b to an operator of clients 91/92 or workstation 93, such as, for example, controllers for printing, emailing, texting, etc. the diagnostic assessment of raw medical imaging data 31a/31b.

To further facilitate an understanding of the inventions of the present disclosure, the following description of FIGS. 8A and 8B teach a training phase and a diagnostic phase for a raw diagnostic domain module and an image diagnostic domain module of the present disclosure. From the description of FIGS. 6 and 7, those having ordinary skill in the art of the present disclosure will appreciate how to apply the present disclosure for making and using numerous and various additional embodiments for training and operating raw diagnostic domain modules and an image diagnostic domain modules of the present disclosure.

Referring to FIG. 8, a training phase 100 of a raw diagnostic domain module 50a involves a construction of dimension reduction pre-processor 51 to process training raw medical imaging data 31a, which is data associated with a previous diagnosis assessment of a reconstructed medical image, to thereby select or extract dimensioned reduction feature vector 53.

Training phase 101 of raw diagnostic domain module 50a further involves a construction of raw diagnostic artificial intelligence engine 52 to process dimensioned reduction feature vector 53 to thereby render the diagnostic assessment of the raw medical imaging data 31a that coincides with the previous diagnosis assessment of the medical image reconstructed from the raw medical imaging data 31a. For example, the risk raw assessment score 41a coincides with the previous diagnosis assessment of the medical image reconstructed from the raw medical imaging data 31a. To this end, artificial intelligence parameters 46a may be added, modified and/or deleted as necessary to adjust raw diagnostic artificial intelligence engine 52 as needed to ensure the diagnostic assessment of the raw medical imaging data 31a coincides with the previous diagnosis assessment of the medical image reconstructed from the raw medical imaging data 31a. Additionally, assessment captions 47 may be added to raw diagnostic artificial intelligence engine 52 to serve as raw risk assessment descriptions 42a.

Still referring to FIG. 8A, diagnosis phase 101 involves an inputting of diagnostic raw medical imaging data 31b into dimension reduction pre-processor 51 to select or extract dimension reduced feature vector 53b, which is inputted into raw diagnostic artificial intelligence engine 52 to thereby render a risk raw assessment score 41b and raw risk assessment descriptions 42b of diagnostic raw medical imaging data 31b. More particularly, diagnostic raw medical imaging data 31b represents undiagnosed data for evaluation by raw diagnostic domain module 50a, especially in a time critical emergency situation.

Referring to FIG. 8B, a training phase 102 of an image diagnostic domain module 70a involves a construction of medical image pre-processor 71 to process training reconstructed medical image 43a, which a previous diagnosed reconstructed medical image, to thereby extract medical image feature vector 73 as known in the art of the present disclosure. In practice, medical image pre-processor 71 is constructed whereby features of medical image feature vector 73 coincide with features of dimensioned reduction feature vector 53 (FIG. 8A).

Training phase 102 of image diagnostic domain module 70a further involves a construction of image diagnostic artificial intelligence engine 72 to process medial image feature vector 73 to thereby render the diagnostic assessment of the reconstructed medical image 43a that coincides with the previous diagnosis assessment of the medical image reconstructed from the reconstructed medical image 43a. For example, the image risk assessment score 41a coincides with the previous diagnosis assessment of the reconstructed medical image 43a. To this end, image diagnostic artificial intelligence engine 72 has the same or equivalent architecture of raw diagnostic artificial intelligence engine 52 (FIG. 8B) whereby artificial intelligence parameters 46b may be added, modified and/or deleted as necessary to adjust image diagnostic artificial intelligence engine 72 as needed to ensure the diagnostic assessment of the reconstructed medical image 43a coincides with the previous diagnosis assessment of the medical image reconstructed from the reconstructed medical image 43a. Additionally, assessment captions 47 may be added to image diagnostic artificial intelligence engine 72 to serve as image risk assessment descriptions 45a.

Still referring to FIG. 8B, diagnosis phase 103 of an image diagnostic domain module 70a involves an inputting of diagnostic reconstructed medical image 43b into medical image pre-processor 71 to extract medical image feature vector 73b, which is inputted into image diagnostic artificial intelligence engine 72 to thereby render a risk raw assessment score 41b and raw risk assessment description 42b of diagnostic reconstructed medical image 43b, which may serve as a validation of a risk raw assessment score 41b and raw risk assessment descriptions 42b of diagnostic raw medical imaging data 31b.

In practice, a raw diagnostic domain module of the present disclosure may be trained for a particular type of medical imaging machine and a particular anatomical region or anatomical organ. For example, FIG. 9 illustrates raw diagnostic domain modules 50b-50e that were trained for a CT machine imaging of a liver, a brain, a thoracic region and a cranial region, respectively. FIG. 9 further illustrates raw diagnostic domain modules 50f-50i that were trained for a MRI machine imaging of lungs, a prostate, a mammary region and a sternum region, respectively. FIG. 9 further illustrates raw diagnostic domain modules 50j-50m that were trained for a X-ray machine imaging of lungs, a prostate, a mammary region and a sternum region, respectively. FIG. 9 further illustrates raw diagnostic domain modules 50n-50g that were trained for an ultrasound machine imaging of lungs, a prostate, a mammary region and a sternum region, respectively.

To further facilitate an understanding of the inventions of the present disclosure, the following description of FIGS. various applications of the inventive principles of the present disclosure as set forth in FIGS. 3-9. From the description of FIGS., those having ordinary skill in the art of the present disclosure will appreciate how to apply the present disclosure for applying the inventive principles of the present disclosure in practice.

Tomographic Imaging: In modern medical CT systems, a gantry revolves around a patient, and on this rotating gantry sits an x-ray source on one side and rows of detector elements on the opposite side. The data acquired by the scanner is referred to as the projection sinogram, representing the x-ray attenuation integrated along the path of the x-ray beam. Subsequently, reconstruction algorithms are applied to the projection data to form images. Tomographic imaging is prevalent in medicine—principles of transmission or emission tomography are used in CT, MRI (magnetic resonance imaging), PET (positron emission tomography), SPECT (single photon emission computed tomography), DOT (diffuse optical tomography), among others. Since all the information necessary to form images are contained in the projection data, it is clear that projections contain sufficient information for diagnosis. However, prior to the present disclosure, the identification of objects of interest (e.g., hemorrhage, tumors) in all these instances is performed not on the projection data, but on the reconstructed images.

The CT projection process is captured mathematically as the Radon transform of the underlying field of x-ray attenuation coefficients. The projection process is such that every localized feature in image-space (e.g., hemorrhage) is transformed into a sinusoid in the sinogram space in FIGS. 10A-10F. While most modern clinical CT scanners use cone-beam x-rays in helical mode to produce multi-row sinograms, for simplicity in the present disclosure, fan-beams projected through axial images to produce projection sinograms.

Figure 10:
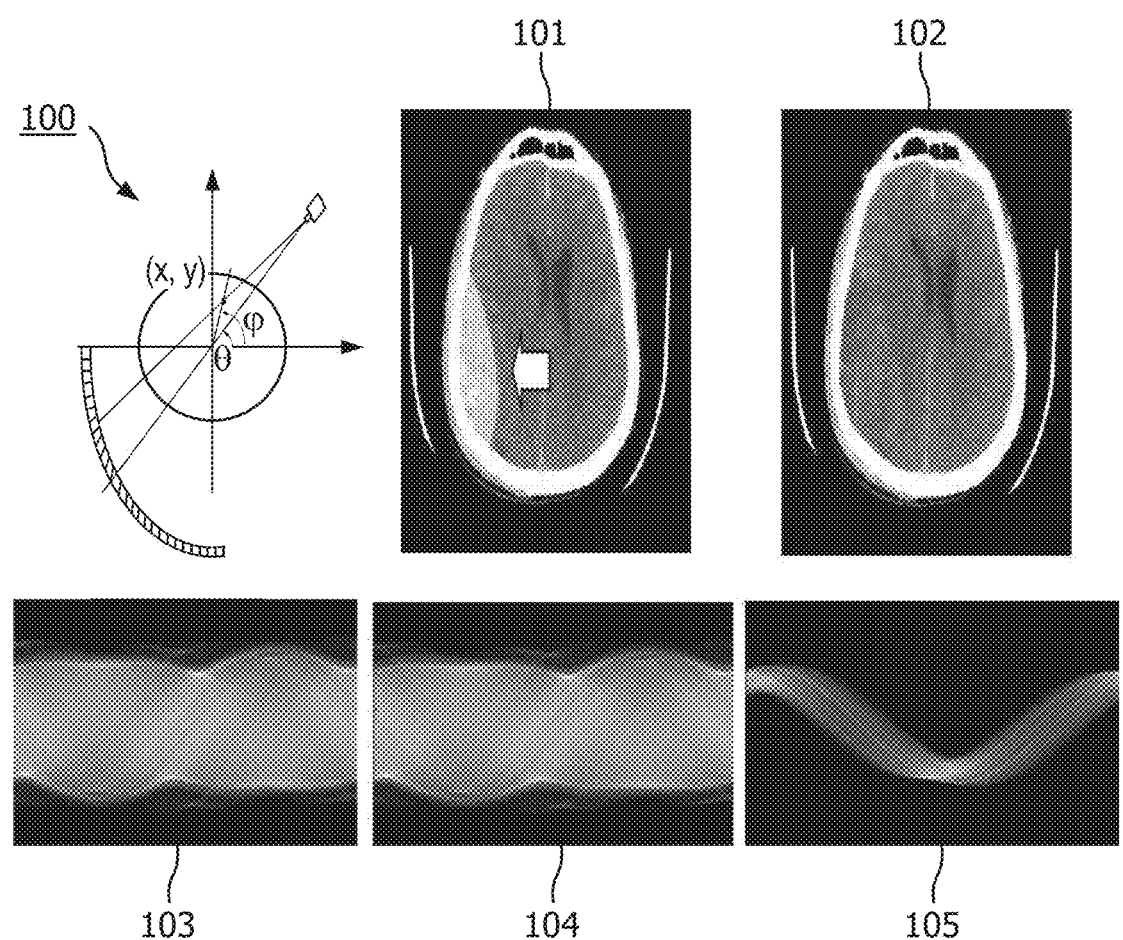
FIG. 10 illustrates exemplary projection data in CT imaging in accordance with the inventive principles of the present disclosure.

More particularly, FIG. 10 illustrates a CT data acquisition geometry 100 whereby, at each angle of rotation $\theta$, the received signal at the detector is related to the line integral of the attenuation coefficients along the path w according to $I_t = I_o \cdot e^{-\int_o^L \mu(w) dw}$, where $I_o$ and $I_t$ are the incident and transmitted beam intensities, respectively, and $\mu(w)$ is the x-ray linear attenuation coefficient along the ray w of path-length L. With rotation angle $\theta$ relative to the body, we can define any point (x,y) within the field of view by $r = \sqrt{x^2+y^2}$, and $\varphi = \tan^{-1}(y/x)$. Then the x-ray from the source through point (x,y) to the detector array is given by the sinusoid $p_\theta = r \cdot \cos(\varphi - \theta)$. FIG. 10 further illustrates a CT image 101 of a large epidural hemorrhage (arrow) in the brain whereby the hemorrhage in CT image 101 is digitally removed in a CT image 102 by replacing pixel values from the contra-lateral side. FIG. 10 further illustrates sinograms 103 and 104 corresponding to CT images 101 and 102, respectively, and a sinogram difference 105 between sinograms 103 and 104, showing the projection of the hemorrhage only. Note that the maximum value of sinograms 103 and 104 are approximately 45,000, and the maximum value of sinogram difference 105 is 1,000.

This embodiment used random projections to reduce the dimensionality of the feature vectors to a more manageable size. Vectors in the original n-dimensional space X is projected onto a k-dimensional subspace Xp via the random projection matrix R (that is, Xp=R·X) where k<<n, and the columns of R are realizations of independent and identically distributed zero-mean normal variables with unit length. While in general a projection matrix needs to have orthogonal columns, one property of high-dimensional datasets is that when the direction of each vector is random, most of the vectors are "nearly" orthogonal, where "nearly" is precisely defined by the Johnson-Lindenstrauss theorem. Because orthogonal basis functions are expensive to compute, random projections provide a computationally efficient approach to reducing feature space dimensionality. For this embodiment, several values of k were examined and acceptable performance with 28,000 dimensions were achieved. Thus, through the use of random projections, the dimensionality of the feature vectors by were reduced ~96.5%.

Given a set of dimensioned reduced feature vectors—one vector corresponding to each projection sinogram—a support vector machine (SVM) is used to determine whether each feature vector represents patient that is normal or has a hemorrhage. More particularly, SVM is a class of algorithms which performs classification by embedding feature vectors in a higher dimensional manifold in such a way so as to maximize the separation between the classes as in graph 106 shown in FIG. 11. For this embodiment, the focus is only on linear SVMs with linear kernels. It's important to note that although the classifier may require significant computations to determine during training, once computed, only a simple dot product is needed to classify each new feature vector.

Figure 11:
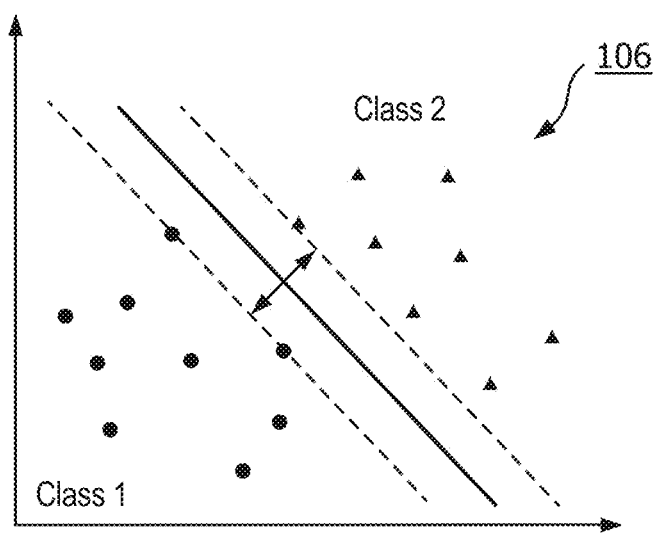
FIG. 11 illustrates an exemplary support vector machine (SVM) in accordance with the inventive principles of the present disclosure.

More particular to FIG. 11, in the training phase of a support vector machine (SVM) classifier, each input vector $x_i$ (i=1, . . . , n) of dimension k is associated with a label $y_i$, where $y_i = +1$ if $x_i$ is from class 1 (normal sinogram), and $y_i = -1$ if $x_i$ is from class 2 (hemorrhage sinogram). The next step is to define a weighting matrix w which defines the hyperplane w·x−b=0 that separates the two classes, shown as the thick line separating classes 1 and 2 in FIG. 11. More specifically, a Lagrange multiplier equation is used to normalize the size of w, subject to the constraint that the labelled training samples are satisfied. The equation which defines w and b is given by (with $\alpha_i$'s the Lagrange multipliers) $L_p = \frac{1}{2}\|w\|^2 - \Sigma_{i=1}^n \alpha_i y_i (x_i \cdot w + b) + \Sigma_{i=1}^n \alpha_i$. That is, $L_p$ is minimized with respect to w and b.

In the diagnostic phase, 224 patient brain CT images (88 normal and 136 hemorrhage) were obtained retrospectively, and subsequently projection sinograms were created. Hemorrhage types consisted of subdural, epidural, and subarachnoid, with sizes ranging from 0.5-190 ml and an average size of 26.2 ml.

Figure 12:
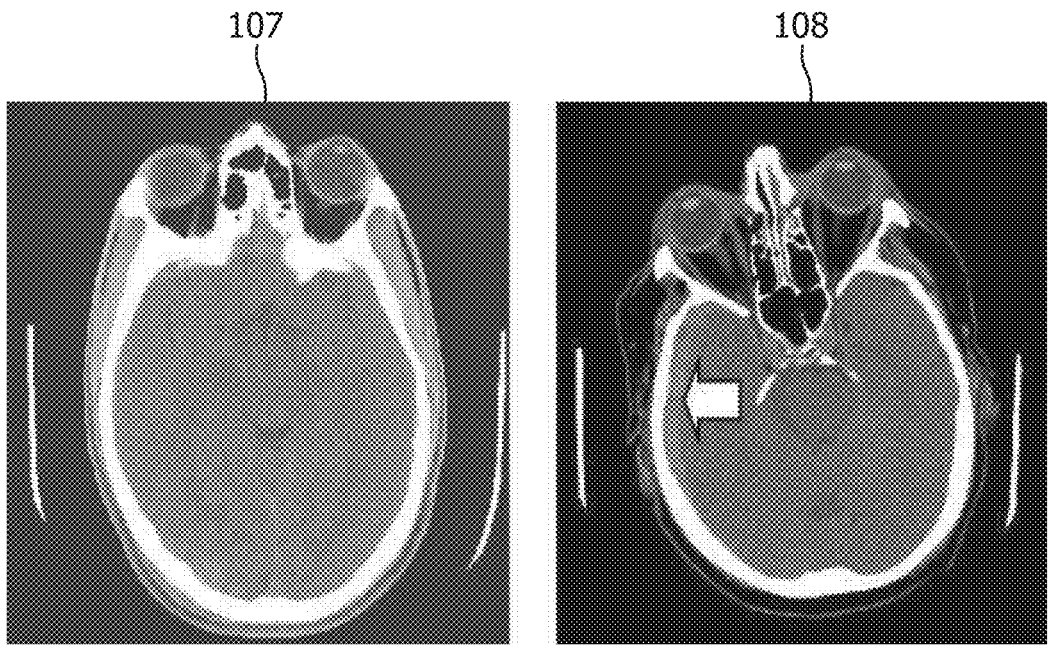
FIG. 12 illustrates an exemplary performance of the SVM of FIG. 11.

FIG. 12 illustrates the classifier performance using real CT data. CT image 107 is an example of a normal CT and CT image 108 is an example of a CT with subdural hemorrhage symbolized by the arrow. The full performance matrix of the SVM classifier averaged over 10 cross validation trials is shown in the following TABLE 1.

TABLE 1

| SVM Diag | True Diagnosis | |
|---|---|---|
| | Normal | Hemorrhage |
| Normal | 38.2% | 4.6% |
| Hemorrhage | 1.1% | 56.1% |
| | 39.3% | 60.7% |

Figure 13:
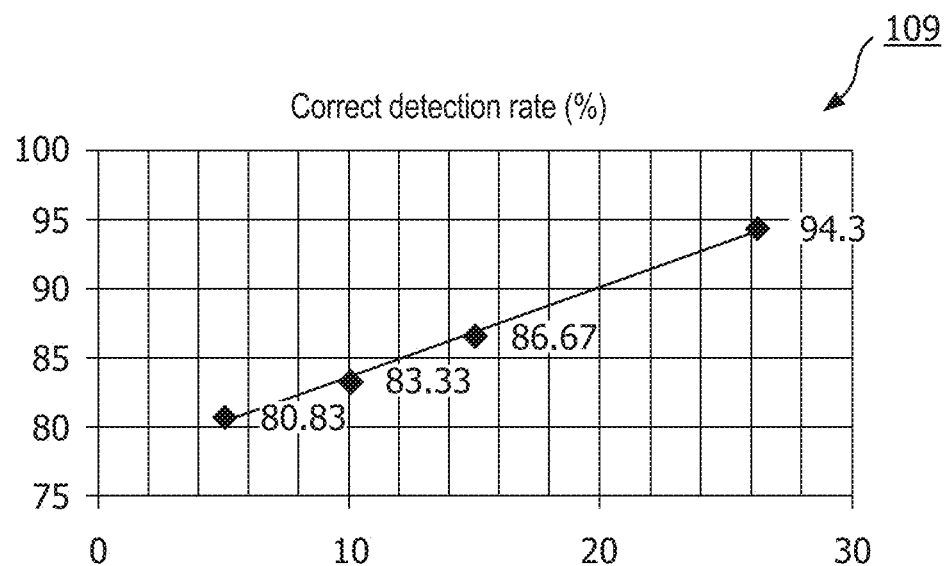
FIG. 13 illustrates an exemplary hemorrhage detection performance of the SVM of FIG. 11.

Results show an overall correct classification rate of 94.3%, with a sensitivity of 92.4%, and a specificity of 97.2%, and FIG. 13 illustrates a graph 109 of hemorrhage detection performance as a function of the size of the hemorrhage, $R^2=0.9963$.

To summarize, in this study, preliminary evidence was obtained that automated diagnosis of intracranial hemorrhage can be performed in the CT projection domain instead of image domain. Performing diagnosis in the projection (raw) domain may seem counter-intuitive since spatially localized anatomical features in images have been transformed into sinusoids. However, with advances in machine learning techniques, and with CT scanners generating increasingly finer resolution and greater volume of data, the inventive principles of the present disclosure provides a new and unique approach to tomographic domain computer-based diagnosis.

Of importance to note is a performance of the system depends upon the size of the hemorrhage encountered, as evidenced by FIG. 13. Although bleeding in the brain is always worrisome, it is worthwhile noting that, at least in the case of hemorrhagic stroke, the hemorrhage size which predicts 30-day mortality outcome is >30 ml. In this context, the inventions of the present disclosure may hold significant promise for rapidly and accurately rendering diagnostic advice for suitable interventions. Additionally, the potential for improving detection sensitivity of the inventions of the present disclosure to smaller hemorrhage may be achieved in retaining more features and through the use of more sophisticated SVM designs.

Figure 14:
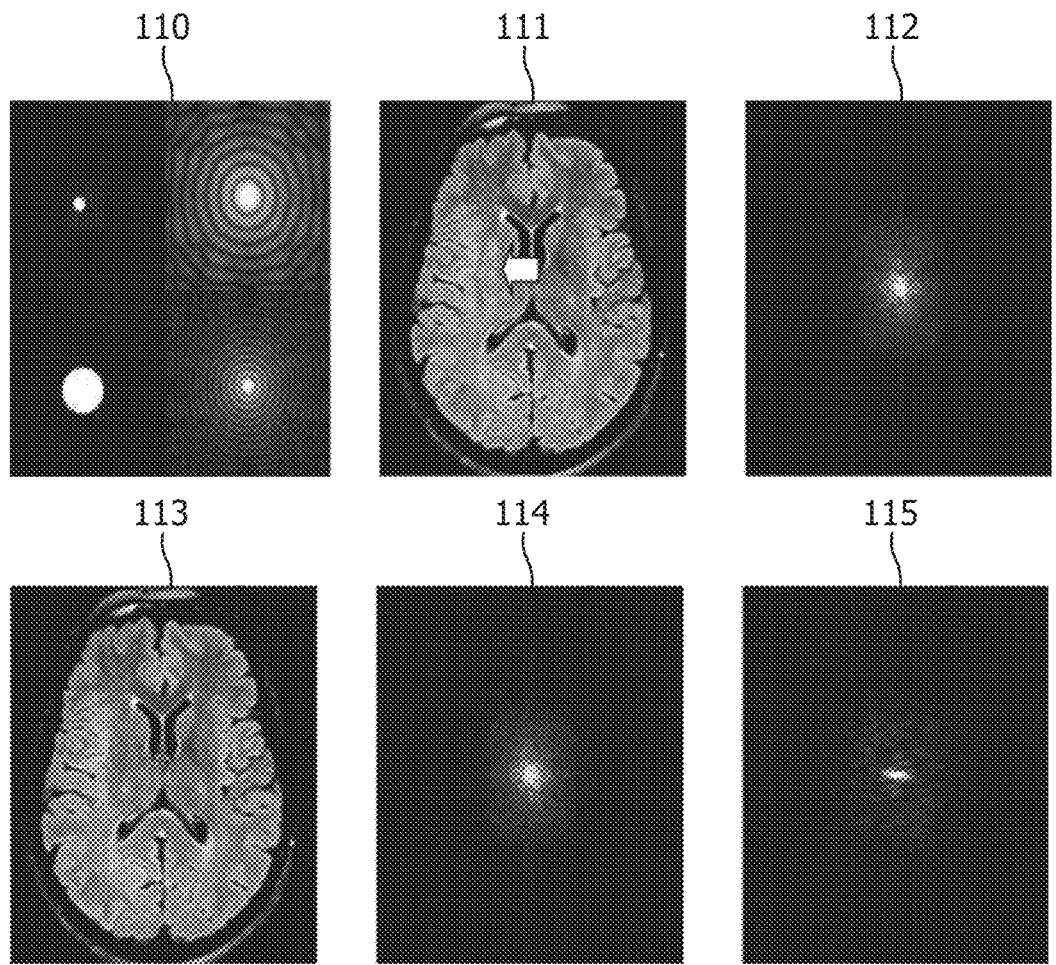
FIG. 14 illustrates exemplary k-space in MRI in accordance with the inventive principles of the present disclosure.

Fourier Style Reconstruction with Deep Neural Networks. To learn clinically relevant features in k-space, a raw diagnostic module of the present disclosure would need to designed to learn diffuse patterns rather than localized abnormalities. For example, a point object in k-pace image 110 of FIG. 14, which has similarities to lesion, would have its information localized in the image but 'diffuse' in k-space. In MR imaging, the relationships between the image and k-space are governed by Fourier theory (e.g. frequency modulation, scaling). This is particularly relevant for many medical imaging problems where the standard approach is to find a small abnormality such as infarcts, tumors, and fractures. This is important because the majority of the image information is irrelevant to the diagnosis. Finding a small localized "signal in the noise" is actually more difficult for a computer than describing a diffuse feature. Typically, this challenge is overcome by using either a two stage approach including localization followed by classification or with attention mechanisms. However, in the acquisition domain a small localized object will have a more diffuse appearance would not require attention mechanisms which are difficult to train. However, the raw diagnostic module of the present disclosure would be need to take in a broader input increasing dimensionality.

More particularly, FIG. 10 illustrates an image 110 showing a relationship of circular objects to their k-space representation, a fluid-attenuated inversion recovery (FLAIR) MRI image 111 showing a subtle asymmetry of the right putamen having an artificially removed lesion for demonstration and a MR image 112 whereby the hyperintense lesion in MR image 111 is digitally removed by replacing pixel values from the contra-lateral side.

FIG. 10 further illustrates k-spaces 113 and 114 corresponding to MR image 111 and MR image 112, respectively, and a k-space differential 115 between k-spaces 113 and 114, showing the frequency response of the lesion only. Note that the maximum value of k-spaces 113 and 114) are 10:1 relative to (f). (Note: k-space is simulated with a simple Cartesian sampling schema).

Figure 15:
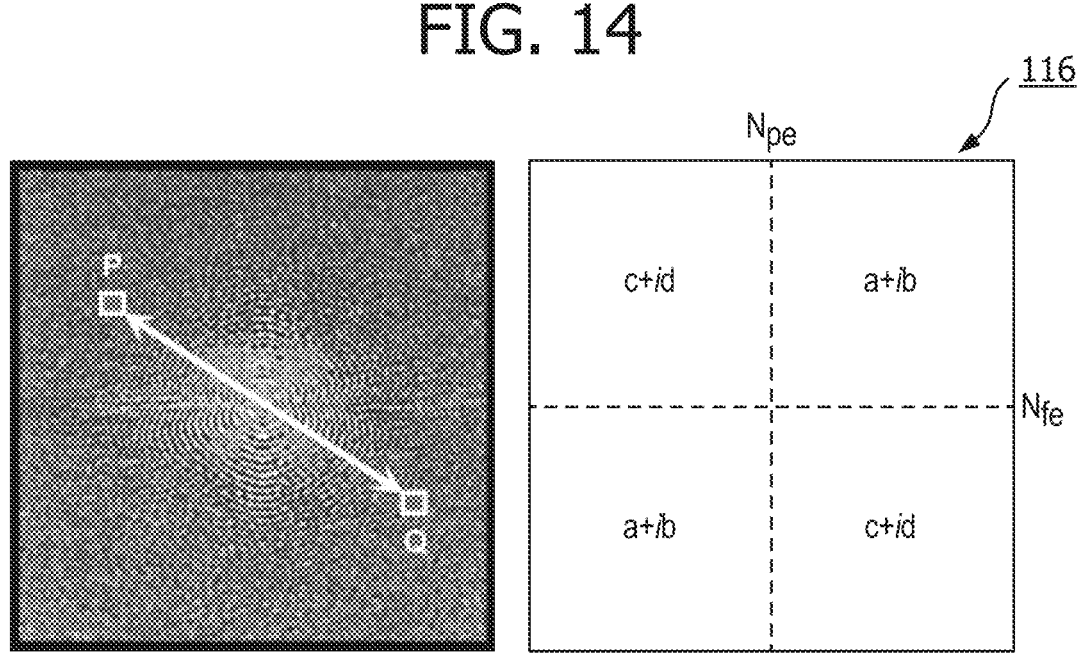
FIG. 15 illustrates exemplary symmetry of k-space in accordance with the inventive principles of the present disclosure.
Figure 16:
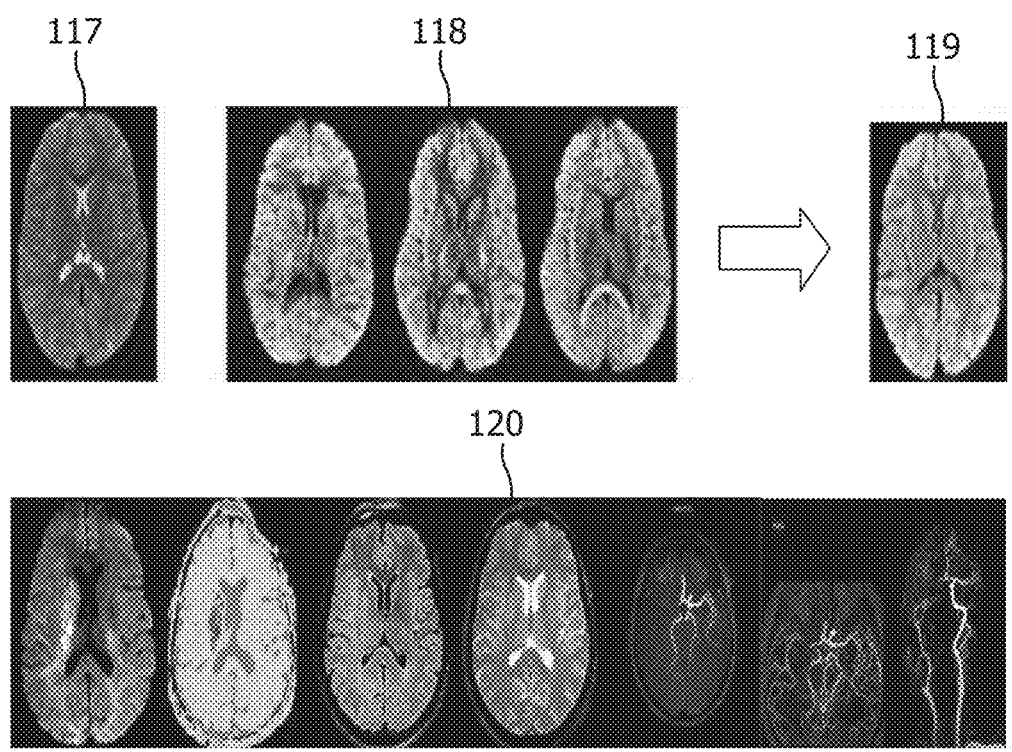
FIG. 16 illustrates exemplary k-space images in accordance with the inventive principles of the present disclosure.

Partial Fourier imaging is common with MRI where as little as one-half of k-space is used to generate an entire MR image. This is feasible due to the redundancy of k-space information. Provided there are no phase errors during data acquisition, k-space has Hermitian symmetry 109 as shown in FIG. 15. For MRI, the present disclosure exploits its k-space symmetry to reduce the feature space dimensionality. More particularly, FIG. 15 highlights the symmetry of K-space. Specifically, conjugate symmetry 109 applies to pairs of points, such as P and Q, that are located diagonally from each other across the origin of k-space. If the data at P is the complex number [a+bi], the data at Q is immediately known to be P's complex conjugate, [a−bi]. $N_{pe}$ is the number of phase encodes and $N_{fe}$ is the number of frequency encodes.

Another differentiating factor between image domain and k-space is the shape of the input, which would need to have two channels (Real and Imaginary) to account for the signal information stored in complex numbers in K-space. In TABLE 2 and TABLE 3, we describe two simple network architectures that could be used for this problem (Training data is required to refine the network design; dropout, regularization, and batch normalization not included). A 2D or 3D design may depend on the pulse sequence or type of anatomy being investigated. This is just one of many AI approaches, where an SVM based approach as described in embodiment 1 or other network architectures could produce a similar result.

TABLE 1

Potential 3D network architecture fork-Space.

| Layer | Activation | Remark |
|---|---|---|
| kspace_input | | Shape = $N_{pe}/2 \times N_{fe}/x$ number of slices × 2 |
| Average Pool | | Down sample z-axis |
| 3D Convolution | ReLu | |
| Maxpooling | — | |
| 3D Convolution | ReLu | |
| 3D Convolution | ReLu | |
| Maxpooling | — | |
| 3D Convolution | ReLu | |
| 3D Convolution | ReLu | |
| Maxpooling | — | |
| Fully Connected | ReLu | |
| Fully Connected | Softmax | |

TABLE 2

Potential 2D network architecture for k-Space.

| Layer | Activation | Remark |
|---|---|---|
| kspace_input | | Shape = $N_{pe}/2 \times N_{fe}/2 \times 2$ |
| 2D Convolution | ReLu | |
| Maxpooling | — | |
| 2D Convolution | ReLu | |
| 2D Convolution | ReLu | |
| Maxpooling | — | |
| 2D Convolution | ReLu | Repeated for each slice, weights are shared |
| 2D Convolution | ReLu | |
| Maxpooling | — | |
| Fully Connected | ReLu | |
| Fully Connected | Softmax | |
| Prediction loss | | Combined loss function – P = 1 − $\alpha \Pi_i(1 - P_i)$ |

The present disclosure here shows an example of T2-weighted Acute Ischemic Stroke as anatomic MR imaging has a more straightforward relationship between the image and k-space. However, this method may also be used to detect an infarction detected with diffusion weighted MR in (hyper) acute stroke or other indirect MR imaging methods, where Image≠FT {K-space}. This is another compelling use case due to the implications on patient's outcome in a short time window and the volume of patients presenting in Emergency Departments with symptoms indicative of ischemic stroke. According to the World Health Organization, 15 million people suffer stroke worldwide each year. Of these, 5 million die and another 5 million are permanently disabled. Ischemic stroke accounts for 88% of these patients). The successful treatment of suspected ischemic stroke patients, requires early diagnosis, fast treatment decisions, and immediate response.

Diffusion weighted imaging (DWI) is a commonly performed MRI sequence for evaluation of acute ischemic stroke, and is sensitive in the detection of small and early infarcts. Conventional MRI sequences (T1-Weighted, T2-Weighted) may not demonstrate an infarct for 6 hours, and small infarcts may be hard to appreciate on CT for days, especially without the benefit of prior imaging. The time for presentation of an infarct on non-enhanced computer tomography is even longer.

Increased DWI signal in ischemic brain tissue is observed within a few minutes after arterial occlusion and progresses through a stereotypic sequence of apparent diffusion coefficient (ADC) reduction, followed by subsequent increase, pseudo-normalization and, finally, permanent elevation. Reported sensitivity ranges from 88-100% and specificity ranges from 86-100%. However, this approach could also be used for acute stroke imaging including diffusion weighted, perfusion, and angiography sequences in addition to anatomical imaging (T2 weighted or FLAIR).

Diffusion weighted images are also acquired in k-space similar to T1 and T2 weighted images. However, to extract the functional status of the tissue often quantified as the Apparent Diffusion coefficient (ADC), it is necessary to acquire multiple k-space images with varying diffusion gradient strengths (varying b-values) as shown in FIG. 15.

More particular to FIG. 15, a creation of an apparent diffusion coefficient (ADC) map 119 via the acquisition of an image 117 with no diffusion weighting ($b_o$) and several images 118 with varying b-values. These image are combined to create the ADC map 119 ($S_{DWI}$) by the following formulas: $S_x=S_o e^{-bDxx}$, $S_y=S_o e^{-bDyy}$, $S_z=S_o e^{-bDzz}$, and $S_{SWI}=3\sqrt{(S_x S_y S_z)}$.

FIG. 15 further illustrates a set 120 of images acquired with scanners used for diffenative diagnosis of acute ischemic stroke as known in the art of the present disclosure. From Left to right, set 102 includes a DWI image, a FLAIR image, a T2-Weighted image, a MRA TOF (no contrast) image and a post-Gd MRA (contrast enhanced).

Because there is an important pixel level correlation, applying the proposed networks to the data and combining the results afterwards would obviously loss important information. Instead, the present disclosure proposes to modified the input to have Shape=$N_{pe}/2 \times N_{fe}/2 \times$b-values, where b-values may be treated as channels or an additional dimension. The complex data could then be captured with the approach, or similar, described by Geberman, N. "On Complex Valued Convolutional Neural Networks" (2016). https://arxiv.org/pdf/1602.09046.pdf, incorporated herein by reference. This approach could be extended to other MR functional scans such DCE or DSC MRI, where the input would have Shape=$N_{pe}/2 \times N_{fe}/2 \times$time.

Figure 17:
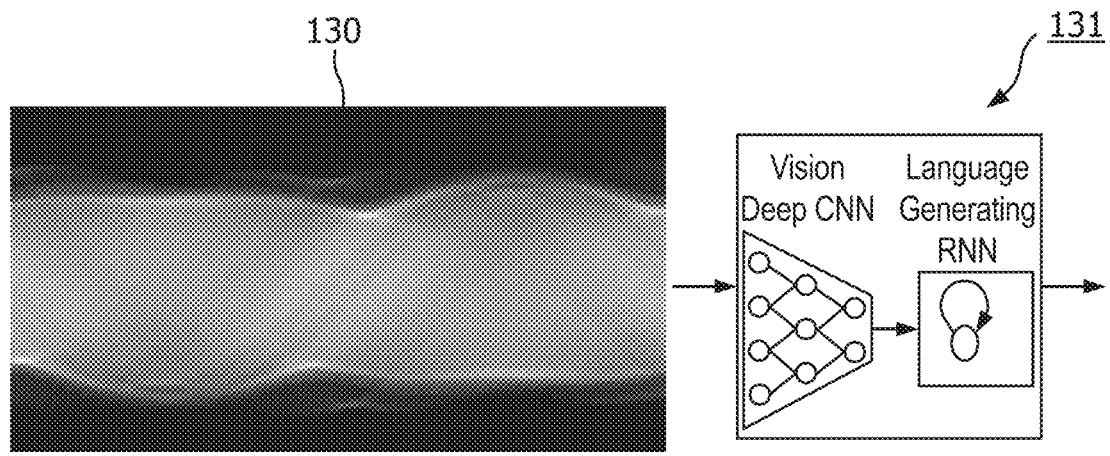
FIG. 17 illustrates an exemplary deep recurrent architecture in accordance with the inventive principles of the present disclosure.

Raw-data to Text to improve clinician acceptance of risk score: FIG. 17 illustrates a first of kind deep recurrent architecture 131 that combines recent advances in machine translation and computer vision that is fine-tuned to medical image characteristics and medical text ontologies. The model 131 was trained with descriptive sentences from medical literature given a medical image utilizing an encoder-decoder neural network. The model 131 works by first "encoding" an image into a fixed-length vector representation via a convolutional neural network (CNN), and then "decoding" the representation into a natural language description. The decoder is a long short-term memory (LSTM) network which is trained as a language model conditioned on the image encoding. Planned work includes improving the accuracy of the model with alternate network architectures and training on targeted clinical datasets as well as extending the CNN to 3D such that volumetric data can be accepted. The present disclosure provide a DNN that is equally capable interpreting relationships in sonograms as in human readable anatomic reconstructions. For example, FIG. 17 provides for an output from deep vision CNN and language generating RNN to produce descriptive text from a sinogram 130 (e.g., "a head CT of ischemic stroke >1 day after onset, showing a hypodense area. Enlargement of left temporal lobe and compression of Sylvian feature"). This would be trained on expert radiologist free text notes.

Figure 18:
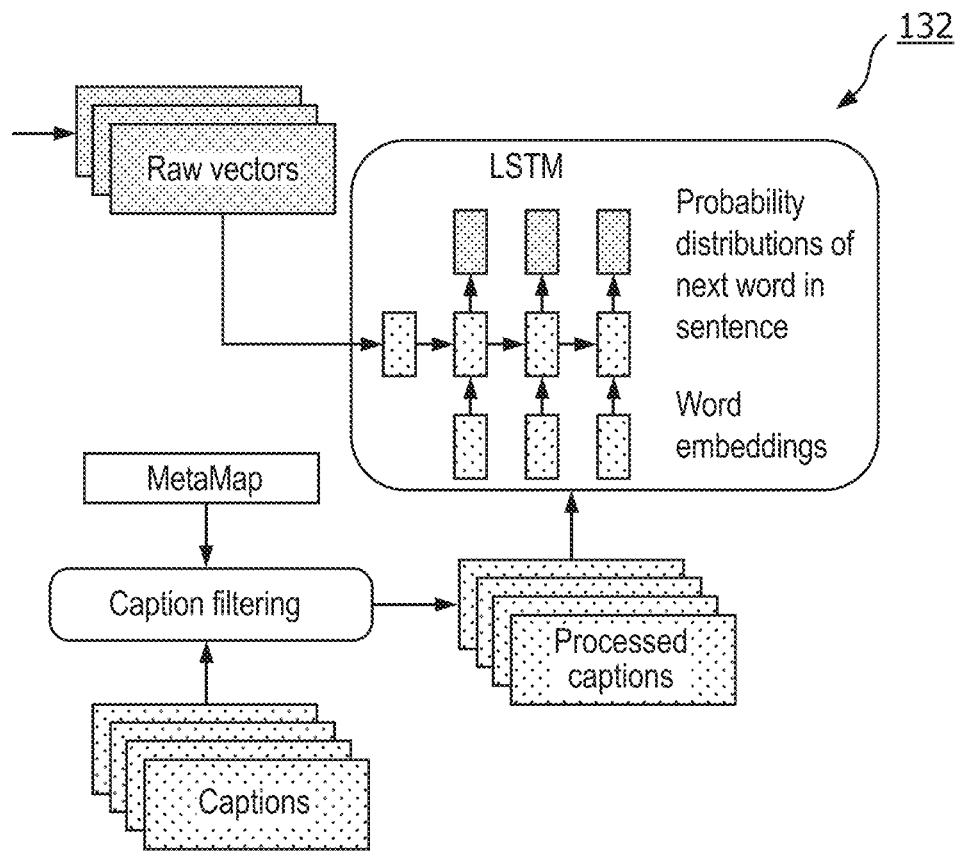
FIG. 18 illustrates an exemplary long short term memory network in accordance with the inventive principles of the present disclosure.

For a generative model, which creates text description of anatomical information from raw data, the inventions of the present disclosure provide for a first use of dimensionality reduction as previously described in the present disclosure followed feature extraction by a CNN. This feature vector be an input into the text generation model 132 as shown in FIG. 18. For training, the dimensioned reduced feature vector would be given as input to the first LSTM cell along with the first caption word, and the sequence of words are similarly passed along to the subsequent LSTM cells. Thus, the image weights are shared across all the LSTM steps during the decoding stage to learn the association between image features and caption words. The series of LSTM cells learns the probabilities of the next word given an input word and raw data such that the resulting model is able to generate a caption (phrase or sentence) when given raw data such as a sonogram or k-space.

Referring to FIGS. 1-19, those having ordinary skill in the art will appreciate the many benefits of the inventions of the present disclosure including, but not limited to, automated diagnosis that is selected or extracted from raw image data with the same or improved accuracy than from the reconstructed medical image directly. For time critical decisions and in settings with limited computation resources, the inventions of the present disclosure are particularly advantageous.

Furthermore, it will be apparent that various information described as stored in the storage may be additionally or alternatively stored in the memory. In this respect, the memory may also be considered to constitute a "storage device" and the storage may be considered a "memory." Various other arrangements will be apparent. Further, the memory and storage may both be considered to be "non-transitory machine-readable media." As used herein, the term "non-transitory" will be understood to exclude transitory signals but to include all forms of storage, including both volatile and non-volatile memories.

While the device is shown as including one of each described component, the various components may be duplicated in various embodiments. For example, the processor may include multiple microprocessors that are configured to independently execute the methods described in the present disclosure or are configured to perform steps or subroutines of the methods described in the present disclosure such that the multiple processors cooperate to achieve the functionality described in the present disclosure. Further, where the device is implemented in a cloud computing system, the various hardware components may belong to separate physical systems. For example, the processor may include a first processor in a first server and a second processor in a second server.

It should be apparent from the foregoing description that various example embodiments of the invention may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A non-transitory machine-readable storage medium encoded with instructions for execution by at least one processor that, when executed by the last one processor, cause the one processor to:
 access raw medical imaging data generated by a medical imaging machine, the raw medical imaging data being arranged for generating a reconstructed medical image by a medical image reconstruction engine;
 generate, by a dimension reduction pre-processor, one or more dimension reduced feature vectors by applying a random projection matrix to the raw medical imaging data, the generated one or more dimension reduced feature vectors respectively having a resultant dimensionality that is a subspace of a raw dimensionality of the raw medical imaging data; and
 generate, by a trained artificial intelligence engine accessing the generated one or more dimension reduced feature vectors, a diagnostic assessment of the raw medical imaging data, wherein the trained artificial intelligence engine is trained by:
  associating training input vectors with one or more respective corresponding classification labels, the classification labels each defining a negative classification and a positive classification;
  for a respective classification label, defining a weighting matrix corresponding to a hyperplane separating the negative classification and the positive classification; and
  normalizing the size of the defined weighting matrix subject to the constraint that the labelled training samples are satisfied.

2. The non-transitory machine-readable storage medium of claim 1, encoded with further instructions to:
 input the raw medical imaging data into a medical image reconstruction engine to generate a reconstructed medical image.

3. The non-transitory machine-readable storage medium of claim 2, encoded with further instructions to:
 input the reconstructed medical image into a medical image pre-processor trained to select or extract at least one medical image feature vector from the reconstructed medical image; and
 input the at least one medical image feature vector into an imaging diagnostic artificial intelligence engine trained to render a diagnostic assessment of the reconstructed medical image.

4. The non-transitory machine-readable storage medium of claim 1, encoded with further instructions to:
 input a reconstructed medical image into a medical image pre-processor trained to select or extract at least one medical image feature vector from the reconstructed medical image; and
 input the at least one medical image feature vector into an imaging diagnostic artificial intelligence engine trained to render a diagnostic assessment of the reconstructed medical image.

5. The non-transitory machine-readable storage medium of claim 1, wherein at least one of:
 the dimension reduction pre-processor is configured to select or extract the at least one dimension reduced feature vector from the raw medical imaging data in correspondence with one of a specified anatomical region or a specified anatomical organ; and
 the raw diagnostic artificial intelligence engine is trained to render the diagnostic assessment of the raw medical imaging data in correspondence with one of the specified anatomical region or the specified anatomical organ.

6. A medical imaging diagnostic method for a medical, the method comprising:
 accessing raw medical imaging data generated by a medical imaging machine, the raw medical imaging data being arranged for generating a reconstructed medical image by a medical image reconstruction engine;
 generating, by a dimension reduction pre-processor, one or more dimension reduced feature vectors by applying a random projection matrix to the raw medical imaging data, the generated one or more dimension reduced feature vectors respectively having a resultant dimensionality that is a subspace of a raw dimensionality of the raw medical imaging data; and
 generating, by a trained artificial intelligence engine accessing the generated one or more dimension reduced feature vectors, a diagnostic assessment of the raw medical imaging data, wherein the trained artificial intelligence engine is trained by:
  associating training input vectors with one or more respective corresponding classification labels, the classification labels each defining a negative classification and a positive classification;
  for a respective classification label, defining a weighting matrix corresponding to a hyperplane separating the negative classification and the positive classification; and
  normalizing the size of the defined weighting matrix subject to the constraint that the labelled training samples are satisfied.

7. The medical imaging diagnostic method of claim 6, further comprising:
 inputting the raw medical imaging data into a medical image reconstruction engine to generate a reconstructed medical image;
 inputting the reconstructed medical image into a medical image pre-processor trained to select or extract at least one medical image feature vector from the reconstructed medical image; and
 inputting the at least one medical image feature vector into an imaging diagnostic artificial intelligence engine trained to render a diagnostic assessment of the reconstructed medical image.

8. The medical imaging diagnostic method of claim 6, further comprising:
 inputting a reconstructed medical image into a medical image pre-processor trained to select or extract at least one medical image feature vector from the reconstructed medical image; and inputting the at least one medical image feature vector into an imaging diagnostic artificial intelligence engine trained to render a diagnostic assessment of the reconstructed medical image.

9. The medical imaging diagnostic method of claim 6, wherein at least one of:
the selecting or extracting by the dimension reduction pre-processor of the at least one dimension reduced feature vector from the raw medical imaging data corresponds to one of a specified anatomical region or a specified anatomical organ; and
the rendering by the raw medical imaging assessment machine of the diagnostic assessment of the raw medical imaging data corresponds to one of the specified anatomical region or the specified anatomical organ.

10. The medical imaging diagnostic method of claim 6, wherein the raw medical imaging data comprises MRI k-space data, CT sonogram data, and/or PET listmode files.

* * * * *